US006238349B1

(12) United States Patent
Hickey

(10) Patent No.: US 6,238,349 B1
(45) Date of Patent: May 29, 2001

(54) METHOD AND APPARATUS FOR NONINVASIVE DETERMINATION OF CARDIAC PERFORMANCE PARAMETERS

(75) Inventor: Donald D. Hickey, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/625,329

(22) Filed: Jul. 25, 2000

Related U.S. Application Data

(62) Division of application No. 09/097,252, filed on Jun. 12, 1998, now Pat. No. 6,120,442
(60) Provisional application No. 60/049,459, filed on Jun. 12, 1997.

(51) Int. Cl.[7] ........................................................ A61B 5/00
(52) U.S. Cl. .......................... 600/486; 600/500; 600/593; 600/526
(58) Field of Search .................................... 600/485, 486, 600/493, 500, 526

(56) References Cited

U.S. PATENT DOCUMENTS

| | | | |
|---|---|---|---|
| 4,517,984 | * | 5/1985 | Perlin .................................. 600/593 |
| 4,981,470 | * | 1/1991 | Bombeck, IV ....................... 600/593 |
| 5,048,532 | * | 9/1991 | Hickey ................................. 600/593 |
| 5,181,517 | * | 1/1993 | Hickey ................................. 600/593 |
| 5,263,485 | * | 11/1993 | Hickey ................................. 600/593 |
| 5,398,692 | * | 3/1995 | Hickey ................................. 600/593 |
| 5,433,216 | * | 7/1995 | Sugrue ................................. 600/593 |

* cited by examiner

Primary Examiner—Robert L. Nasser
(74) Attorney, Agent, or Firm—James C. Simmons

(57) ABSTRACT

Apparatus and method for noninvasively determining cardiac performance parameters including 1) lengths of systolic time intervals, (2) contractility index, (3) pulse amplitude ratios while performing the Valsalva maneuver, (4) cardiac output index, and (5) a pulse wave velocity index. A catheter having at least one balloon is inserted into the esophagus and pressurized and positioned adjacent the aortic arch to sense aortic pressure. The effects of aortic pressure on the balloon are utilized to determine at least one of the cardiac performance parameters. The catheter may include a second balloon which is spaced from the aortic balloon a distance such that when the second balloon is in a position adjacent the left atrium to sense left atrial pressure the aortic balloon is in a position adjacent the aortic arch to sense aortic pressure, this distance being related to the distance between the left atrium and aortic arch in most adult persons.

5 Claims, 30 Drawing Sheets

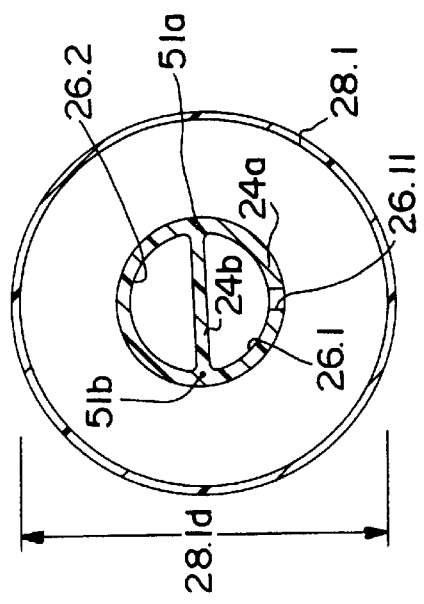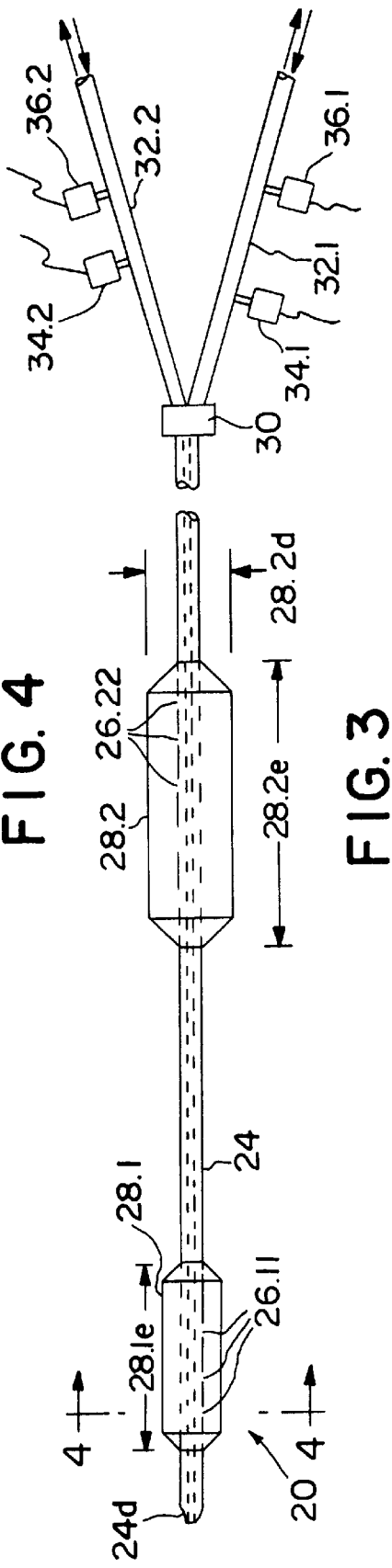

METHOD AND APPARATUS FOR NONINVASIVE DETERMINATION OF CARDIAC PERFORMANCE PARAMETERS

This is a division of application Ser. No. 09/097,252, filed Jun. 12, 1998, now U.S. Pat. No. 6,120,442, which is incorporated herein by reference.

Priority of co-pending U.S. provisional patent application Ser. No. 60/049,459, filed Jun. 12, 1997, is hereby claimed. This provisional application is hereby incorporated herein by reference.

TECHNICAL FIELD

The present invention relates generally to an apparatus and method for noninvasive monitoring of one or more cardiac performance parameters, and more particularly to a method and an apparatus which includes a catheter which may be positioned in the esophagus and associated apparatus for monitoring cardiac performance.

BACKGROUND OF THE INVENTION

The diagnosis and care of patients with cardiovascular disease critically depends on information about the pumping ability of the heart. For example, the priming pressure of the left ventricle of the heart, typically obtained by measurement of left atrial pressure, indicates, when abnormal, a mismatch between volume capacity of the vascular system and the circulatory blood volume.

Since the early 1970's, the flow-directed pulmonary artery balloon catheter (a.k.a. the Swan-Ganz catheter) has been the standard for bedside hemodynamic monitoring. It yields cardiac output by thermodilution as well as an estimate of mean left atrial pressure. However, under certain conditions, the pressure readings may not faithfully reflect left atrial pressure (R. RAPER et al, "Misled by the Wedge" *Chest*, March 1986, pp. 427–434). This invasive technique is personnel intensive and costly since the catheter must be inserted and used in a critical care area or operating room, and it has been associated with infection, arrhythmias, and death (E. ROBIN et al, "The Cult of the Swan-Ganz Catheter", *Annals of Internal Medicine*, Sept. 1985, vol. 103, pp. 445–449). Its use is further limited since it only provides non-automated intermittent measurements, and the catheter should, for safety reasons, only be left in the patient for a few days.

My U.S. Pat. Nos. 5,048,532; 5,181,517; 5,263,485; 5,398,692; 5,551,439; 5,570,671; and 5,697,375, all of which patents are incorporated herein by reference, disclose noninvasive methods and apparatus which includes a catheter containing an inflatable balloon insertable into the esophagus for placement adjacent the left atrium, and associated equipment for making determinations of mean left atrial and mean left atrial transmural pressures. A second catheter containing a second balloon may be used therewith for determining esophageal pressure, which is then added to the mean left atrial transmural pressure to obtain a determination of mean left atrial pressure. Alternatively, a single balloon is used for both purposes wherein the single balloon is moved up the esophagus to measure esophageal pressure and then moved back to the left atrial position. The catheter may also include an esophageal stethoscope and/or an esophageal temperature sensor contained within a protective pouch which surrounds the catheter.

In accordance with one method of positioning the balloon as discussed in my aforesaid U.S. Pat. No. 5,570,671, an electrode means is attached to the catheter just above the balloon to obtain a cardiogram at each of a series of incremental depths as the electrode is moved lengthwise within the esophagus, the esophageal depth at which the balloon is positioned being that which corresponds to the incremental electrode depth at which the electrogram therefor shows the greatest negative portion length of the largest absolute value segment of the respective "p" wave.

However, suitably monitoring a patient's heart condition requires, of course, more than determining the mean left atrial and mean left atrial transmural pressures. Impedance cardiography, which depends on attaching a number of electrodes to the chest, yields continuous readouts of cardiac output, the blood flow generated by the heart. Many researchers consider that this method is unreliable for absolute values but good for relative changes. This device can also provide systolic time intervals. The systolic time interval includes the duration of two phases of ventricular activity: the pre-ejection period (PEP) and the left ventricular ejection time (LVET); PEP refers to the time spent by the ventricle increasing pressure on the volume of blood in it before ejection of the blood into the aorta, and LVET is the duration of the ejection phase. These time intervals are used in various combinations to gauge ventricular performance. For instance, a long PEP is seen when the heart is pumping against increased resistance. Also, the ratio PEP/LVET is known to decrease as cardiac output increases. However, this impedance cardiography method is unable to measure pressures or assess valvular function and furthermore does not work well on the critically ill.

Electrocardiographic analysis of the heart's beating frequency and rhythm allows conclusions about the efficiency of the pump (heart). For instance, an abnormally high beating frequency will preclude effective priming of the pump. In addition, the chambers of the heart must act in synchrony for efficient pumping and, for instance, atrial fibrillation will degrade cardiac output.

Transthoracic and transesophageal echocardiography are excellent techniques for evaluation of valvular function of the heart with respect to leakage and resistance to flow and ventricular pumping action and systolic time intervals. However, the equipment is expensive, the method is very personnel intensive, and the esophageal probe, being large in diameter (perhaps about 9 or 10 mm) is uncomfortable and requires sedation of the patient. This technique also does not lend itself to continuous unattended monitoring of the patient.

Esophageal ultrasound Doppler flow-probe technique provides a good analysis of flow velocity in the descending aorta but gives only partial information about cardiac function. This technique also requires a trained operator. Although it can provide continuous monitoring, small position changes in the probe may make readings unreliable.

Phonocardiography is carried out by placing one or more microphones on the patient's chest. It can give a good analysis of valvular function, but it is susceptible to interference by extraneous sound sources.

Carotid plethysmography offers a qualitative representation of the carotid artery pulse and is used in combination with electrocardiography and phonocardiography to produce systolic time intervals. The method is, however, personnel intensive and not useful for continuous monitoring.

U.S. Pat. Nos. 4,094,308 and 5,086,776 suggest noninvasive methods for sensing cardiac performance. However, these methods are not sufficiently reliable and/or are personnel intensive and/or do not suitably allow continuous automated monitoring of the patient.

The combination of a sphygmomanometer (the common blood pressure cuff), a Swan-Ganz catheter, a phonocardiograph, a carotid plethysmograph, and an electrocardiograph has provided a comprehensive evaluation of cardiac contractility. See "An Indirect Method of Evaluation of Left Ventricular Function in Acute Myocardial Infarction" by C. Agress et al, *Circulation*, vol. XLVI, Aug. 1972, pp. 291–297. The maximum rate of left ventricular pressure change as a function of left ventricular end diastolic pressure (which equals mean left atrial pressure) has been used to determine cardiac pumping function in patients with myocardial infarction and acute coronary insufficiency with marked predictive value for survivors and non-survivors. Unfortunately, this invasive method suffers from being complicated and cumbersome and carries the risks inherent in cardiac catheterization.

OBJECTS AND SUMMARY OF THE INVENTION

It is accordingly a principal object of the present invention to noninvasively determine cardiac performance parameters on a real time basis using novel apparatus and measuring techniques.

More specifically, it is an object of this invention to noninvasively and reliably determine mean left atrial and mean left atrial transmural pressures.

It is a further object of this invention to noninvasively measure systolic time intervals.

It is a still further object of this invention to noninvasively obtain a contractility index (dp/dt/MLAP).

It is a further object of this invention to noninvasively obtain a measure of pulse amplitude ratios while performing the Valsalva maneuver.

It is a further object of the present invention to noninvasively obtain an index of cardiac output.

It is a further object of this invention to noninvasively measure pulse wave velocity.

It is another object of the present invention to provide apparatus therefor which is reliable, inexpensive, easy to use, allows continuous automated monitoring of the patient, and can be employed by paramedical personnel with minimal training.

In order to noninvasively obtain at least one cardiac performance parameter, in accordance with the present invention, a catheter including at least one inflatable balloon is provided for insertion into the esophagus, means is provided for pressurizing the balloon, and means is provided for positioning the balloon to sense aortic pressure on the balloon so that, with use of associated apparatus, at least one cardiac performance parameter may be obtained.

In order to provide a single noninvasive instrument for obtaining information regarding both left atrial and aortic pressures for determining cardiac performance parameters, in accordance with the present invention, a catheter, with which an ECG and an automatic blood pressure cuff or other suitable means for measuring blood pressure and other associated apparatus may be used, is provided which is insertable into the esophagus and which includes at least two inflatable balloons. Means is provided for pressurizing the balloons. The balloons are spaced apart so that when one balloon is positioned adjacent the left atrium the other balloon is positioned adjacent the aortic arch. Means utilizing effects of left atrial and aortic pressures on the respective inflated balloons is provided for obtaining determinations of as well as continuously monitoring cardiac performance parameters including, in addition to mean left atrial and mean left atrial transmural pressures, one or more of (1) lengths of systolic time intervals, (2) contractility index, (3) pulse amplitude ratios while performing the Valsalva maneuver, (4) cardiac output index, and (5) a measurement of pulse wave velocity.

These and other objects, features, and advantages of this invention will become apparent to those skilled in the art after a consideration of the following detailed description taken in conjunction with the accompanying drawings wherein the same reference numerals denote the same or similar parts or items throughout the several views and in which a preferred embodiment of this invention is illustrated.

BRIEF DESCRIPTION OF THE DRAWINGS

FIG. 3 is a schematic view of the catheter.

FIG. 4 is a sectional view taken generally along the line 4—4 in FIG. 3.

DETAILED DESCRIPTION OF THE PREFERRED EMBODIMENT IN GENERAL

Figure 1:
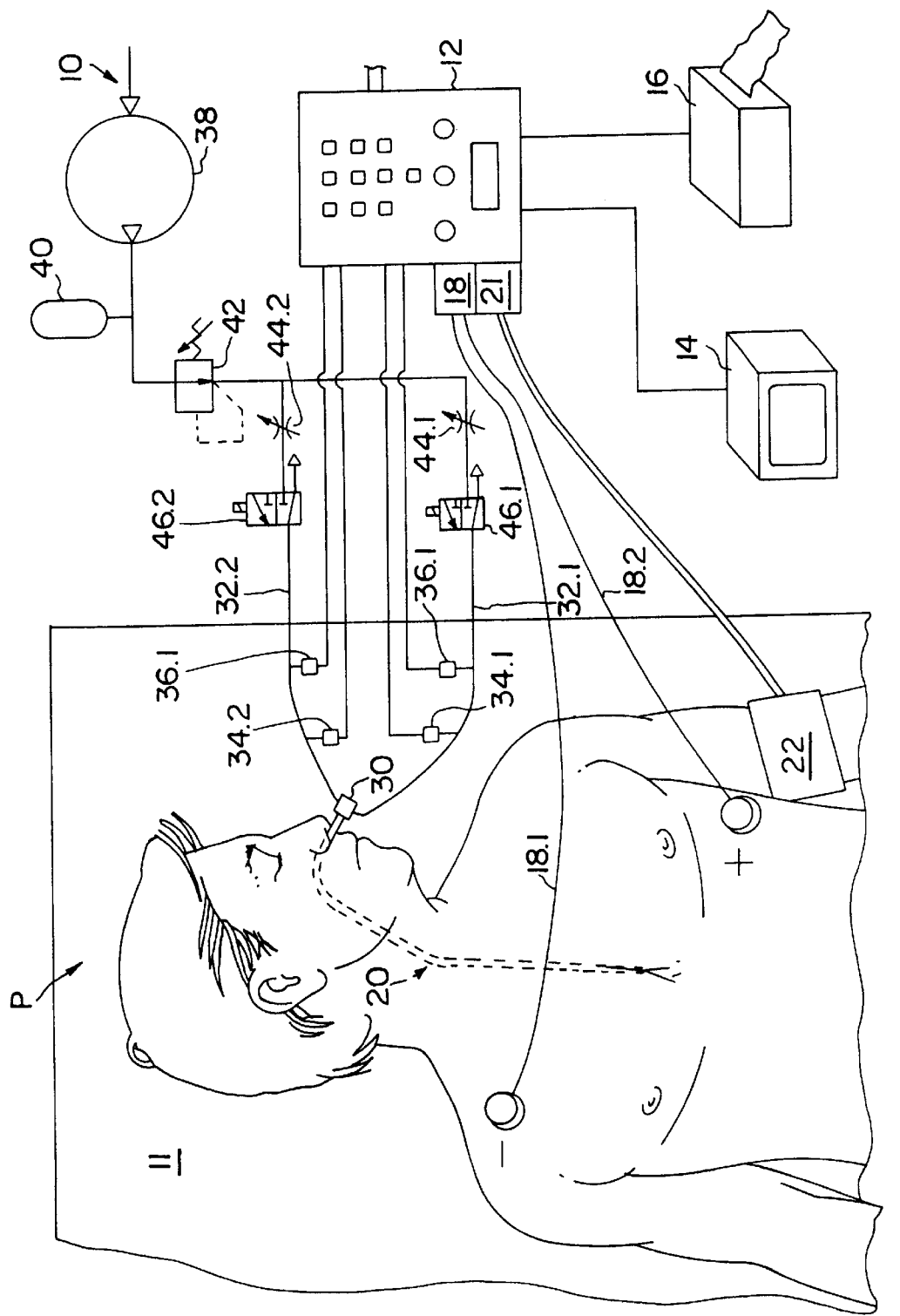
FIG. 1 is a view of a supine patient associated with the apparatus of the present invention.
Figure 2:
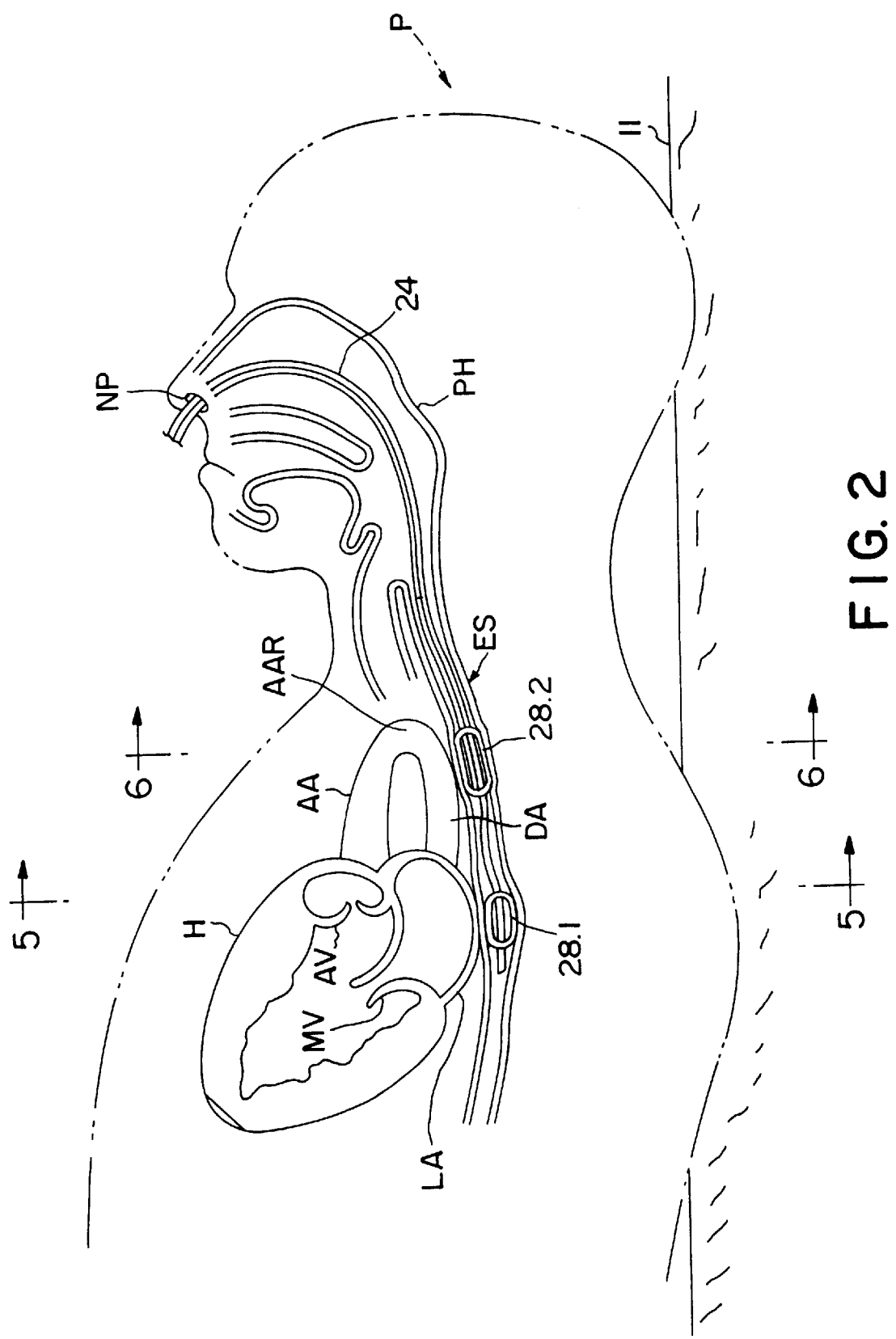
FIG. 2 is a partial left lateral sectional view of the patient taken along the mid-sagittal plane and showing a partially developed esophageal catheter which embodies the present invention.

Referring to FIGS. 1 to 3, the cardiac performance apparatus for noninvasive monitoring, indicated generally at 10, is shown associated with a person P, who may be a patient in a cardiac care setting. The person P is shown in a supine position on a hospital bed, gurney, operating table or the like, which support is indicated at 11. The apparatus includes, as its principal components, a computer including controlling and information processing means 12, and information display apparatus including a CRT 14 and a recorder 16. The controlling and information processing means, which includes a computer, further includes an electrocardiograph (ECG) 18 conventionally having leads 18.1 and 18.2 and a ground lead (not shown), and an automatic sphygmomanometer 21 which is interconnected with a blood pressure cuff 22. The cardiac performance apparatus for non-invasive monitoring additionally includes an esophageal catheter, indicated generally at 20. The automatic sphygmomanometer and blood pressure cuff are of conventional design and will not be described further. The ECG is also of conventional design. While other suitable leads, such as limb leads, could be employed with the ECG, in most cases it will only be necessary to use "lead II" (which is the signal produced by negative lead 18.1 and positive lead 18.2 when applied to the patient in the manner shown). Lead II will produce a good visualization of the P waves, which will be used for timing purposes as set forth below. While lead 18.1 is shown connected to the upper right chest, it may be connected to the shoulder, or right arm. Similarly, the positive lead 18.2 is shown associated with the lower left chest, but it may be connected to the upper left abdomen, or to the left lower leg. The trunk positions are the standard positions used for continuous monitoring in hospitals and by paramedics and Emergency Medical Technicians.

Now, with reference to FIGS. 3 and 4, it can be seen that the catheter 20 includes an integral double lumen flexible tube 24 having an outer wall 24a and an inner wall or partition 24b. These walls define lumens 26.1 and 26.2, which are separated from each other by the inner wall 24b so that fluid (typically air) entering one lumen cannot enter the other lumen. The tubing 24 is preferably an extruded biocompatible generally non-elastic plastic such as, for example, Dow Pellethane 3883-80AE material with 20% barium sulfate and 1% titanium dioxide, and has a diameter of perhaps about 0.13 inch (3.3 mm). The thickness of the outer wall 24a and of the partition 24b may perhaps be about 0.015 inch. On the distal end portion of the tube are mounted a pair of spaced apart balloons 28.1 and 28.2, respectively. The distal end of the double lumen tube 24 terminates at a closed end, illustrated at 24d, beyond the distal balloon 28.1, which end is suitably closed and/or sealed such as by heat seal, epoxy, or the like. Closed end 24d is located perhaps about 1.5 cm beyond the distal balloon 28.1. The upper or proximal end portion of the tube 24 is provided with a suitable coupling 30. The coupling 30 connects the lumens 26.1 and 26.2 to substantially identical fluid lines 32.1 and 32.2, respectively, for flow communication therebetween. Each of the lines 32.1 and 32.2 is interconnected with a pressure compensated microphone (34.1 and 34.2, respectively) and a pressure transducer (36.1 and 36.2, respectively), as discussed hereinafter. Each of the lines is also connected to a source of fluid under substantially constant pressure, such as compressor 38 (FIG. 1) through suitable valves for pressurization of the respective balloon. In order to reduce dead space and eliminate the need for a stepping motor, the compressor 38 outlet is connected to an accumulator 40 and a pressure regulating valve 42. Downstream, each line 32 may be connected via needle valve 44 and a solenoid operated valve 46. The flow through the needle valves may be suitably timed to obtain the desired balloon pressures. The balloons may alternatively be connected to separate pressure sources or to other suitable pressure sources such as described in my aforesaid patents. The fluid conveying apparatus, which includes fluid lines 32, coupling 30, and valves 42, 44, and 46, is referred to as the "MLAP machine" in the flow charts of FIGS. 22 to 25.

The tubing 24 passes through openings in the distal and proximal ends of each of the balloons 28.1 and 28.2, which openings are sealed to the tube in an air tight manner so that each of the balloons can be inflated. The balloons are composed of polyurethane film or other suitable material which is generally non-elastic yet highly compliant. When inflated, the balloons 28.1 and 28.2 have diameters, illustrated at 28.1d and 28.2d, respectively, of perhaps about 8 mm and 11 mm, respectively and have suitable overall lengths as described hereinafter. Since the balloons are deflated during insertion of the catheter and since the catheter is otherwise of small diameter, the catheter may be easily inserted without undue discomfort to the patient. To provide for flow between the balloon and the source of fluid under pressure, inflation openings are provided in the lumen wall portions (in the tube outer wall 24a) which are within the balloons respectively. Thus, there are perhaps three longitudinally spaced 18 gauge (about 0.033 inch diameter) openings 26.11 extending through the wall portion 24a of lumen 26.1 which lies within the distal balloon 28.1. Similarly, there are perhaps four longitudinally spaced 18 gauge openings 26.22 extending through the wall portion 24a of lumen 26.2 which lies within the proximal balloon 28.2. The number and size of such openings may vary. In addition to providing flow means for pressurization of the respective balloons, the openings are provided to facilitate, when the balloons are properly positioned in the esophagus, as discussed below, transmission to the pressure compensated microphones 34.1 and 34.2 of sound waves from the mitral and aortic valves, respectively, for listening thereto and/or obtaining analog or digitized representations thereof.

The pressure transducers 36.1 and 36.2 process pressure waves from the balloons 28.1 and 28.2, respectively, in a manner described in my aforesaid patents. Similarly, microphones 34.1 and 34.2 process sound waves from the balloons 28.1 and 28.2, respectively, in a manner similar to that described in my previous patents. The signals from transducers 36.1 and 36.2, microphones 34.1 and 34.2, ECG leads 18.1 and 18.2, and pressures from blood pressure cuff 22 are suitably processed by the controlling and information processing means 12, which is programmed to suitably process the information to obtain and display the outputs described hereinafter on display apparatus 14 and 16, using principles commonly known to those of ordinary skill in the art to which this invention pertains.

Figure 5:
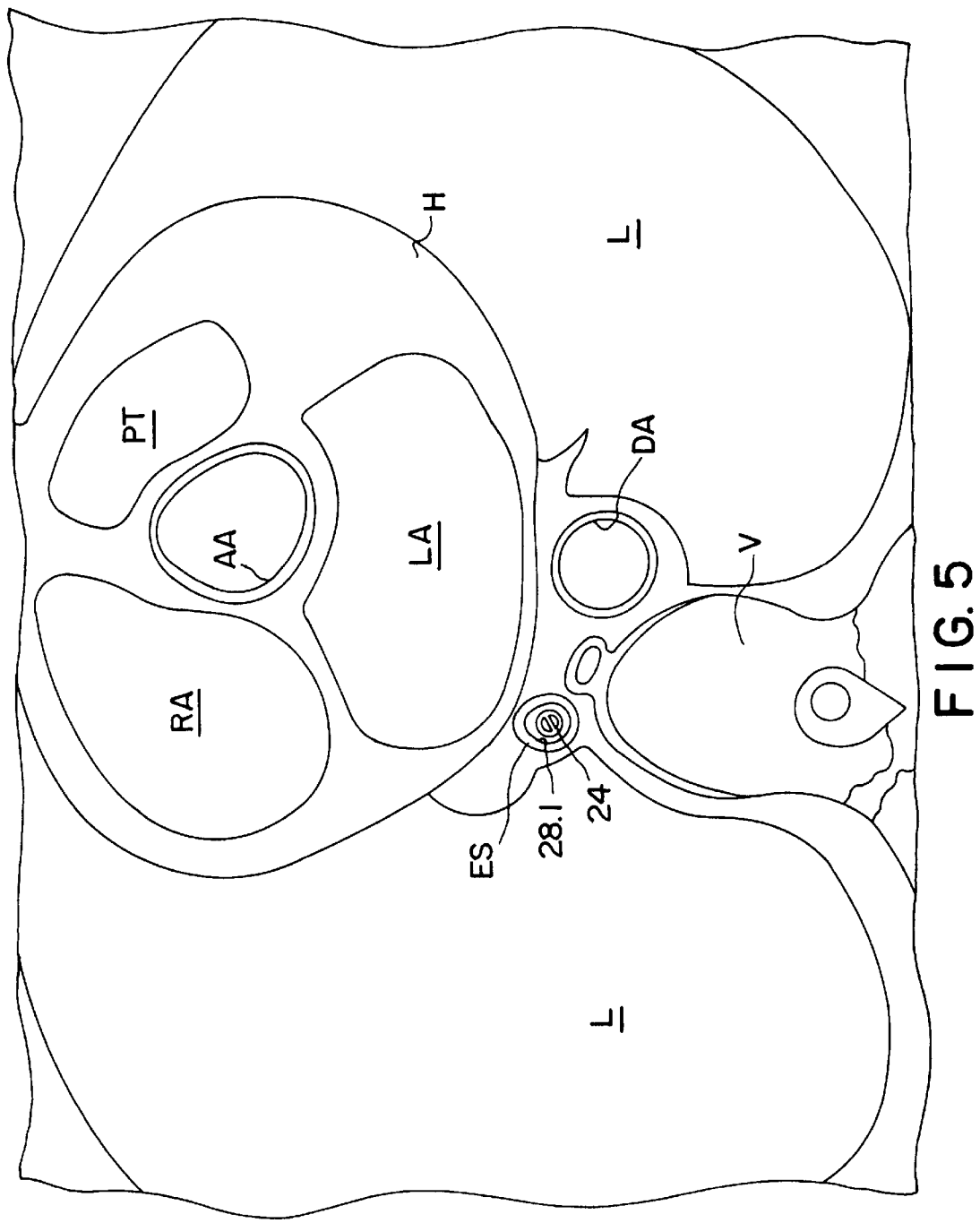
FIGS. 5 and 6 are sectional views taken generally along the lines 5—5 and 6—6 respectively in FIG. 2.
Figure 6:
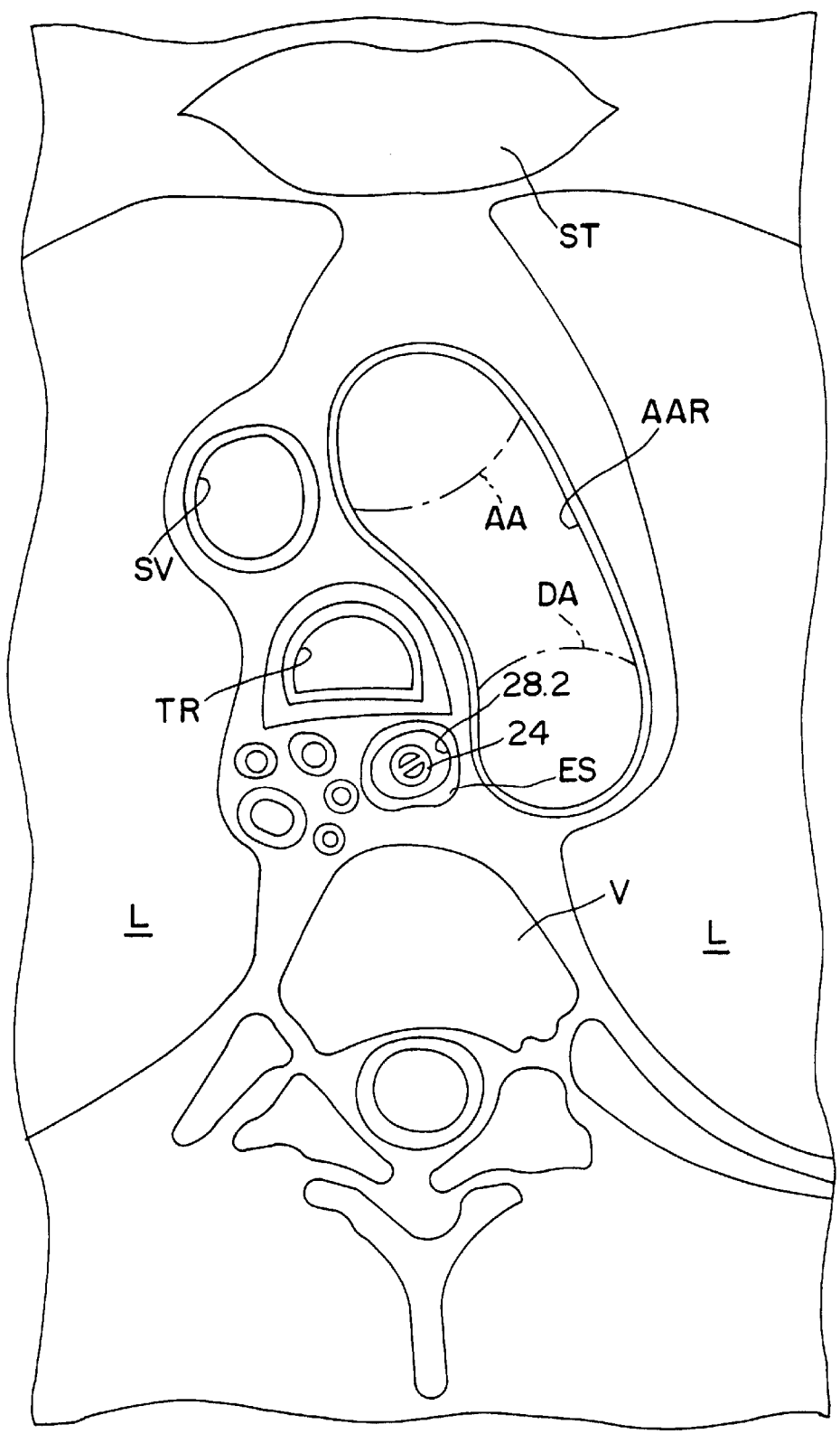

Referring to FIGS. 2, 5, 6, and 7, there is illustrated the placement of the balloons 28.1 and 28.2 within the esophagus ES of a person P for the purpose of noninvasively obtaining and monitoring cardiac performance parameters, as hereinafter discussed, in accordance with the present invention. FIG. 5 illustrates the relationship of the esophagus ES to the left atrium LA and right atrium RA of the heart H, ascending aorta AA, lungs L, pulmonary trunk PT, descending aorta DA, and vertebrae V at the position of placement of distal or left atrial balloon 28.1 within the esophagus ES, and illustrates this balloon adjacent the left atrium LA. The mitral valve MV and aortic valve AV of the heart H are illustrated in FIG. 2, which also illustrates the relationship of the left atrium LA to the aortic arch AAR along the length of the esophagus ES. FIG. 6 illustrates the relationship of the esophagus ES to the aortic arch AAR, sternum ST, superior vena cava SV, trachea TR, and vertebra V at the position of placement of proximal or aortic balloon 28.2 within the esophagus ES, and illustrates this balloon 28.2 adjacent the aortic arch AAR.

Figure 7:
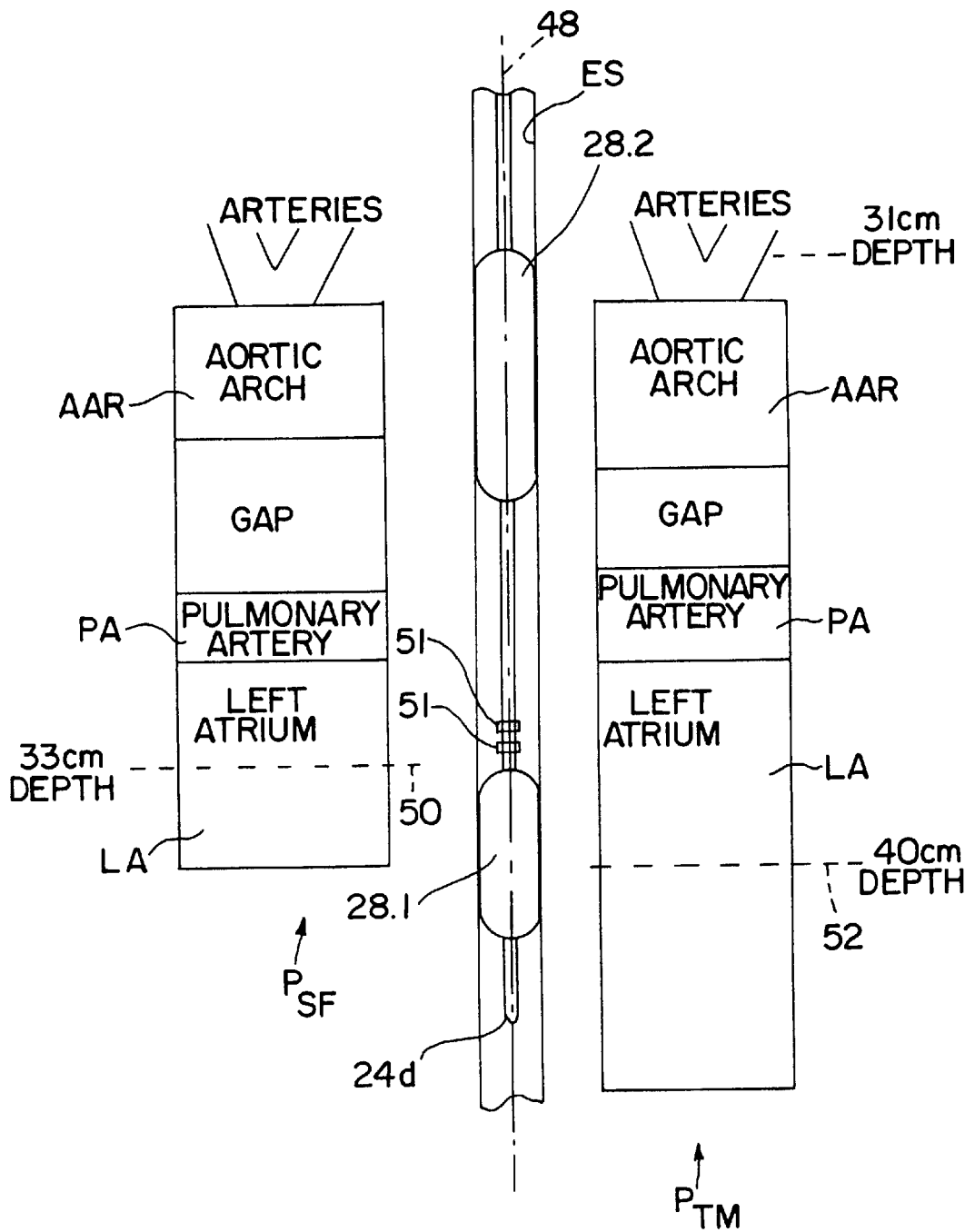
FIG. 7 is a schematic view of a portion of the catheter in the esophagus and illustrating its relation to the left atrium and aortic arch in a tall male adult to the right of the vertical centerline of the figure, and in a short female adult to the left of the vertical centerline, the illustration of the left atrial/aortic arch relationships along the esophagus being drawn to scale in a direction along the length of the esophagus.

The catheter 20, which has a suitable length, which is preferably at least about 80 cm.(from the coupling 30 to the distal end), is inserted distal end 24d first through nasal passage NP, pharynx PH, then into the esophagus ES. If desired, the catheter may alternatively be inserted through the mouth. The tubing 24 desirably has markings (not shown), such as a marking at each centimeter along its length to indicate the distance from the end 24d so that the balloons can be properly positioned as discussed hereinafter. Although the esophagus ES is illustrated in FIGS. 2 and 7 open over its length for ease of illustration, it is of course well known to those of ordinary skill in the art to which this invention pertains that the esophagus is normally collapsed and closes about any objects such as the catheter contained therein. When the catheter is inserted to its proper depth, balloon 28.1 will be positioned underneath (when the subject is in a supine position) and adjacent the left atrium LA of the heart H as shown in FIGS. 2, 5, and 7.

In accordance with the preferred embodiment of the present invention, the balloons 28.1 and 28.2 are spaced apart on the tubing 24 a distance of, for example, about 4 cm and have lengths (suitable lengths as illustrated in FIG. 3) so that, when lower or distal balloon 28.1 is adjacent the left atrium, illustrated at LA in FIGS. 2, 5, and 7, the upper balloon 28.2 is adjacent the aortic arch, illustrated at AAR in FIGS. 2, 6, and 7, and generally below the aortic arch over a substantial portion thereof, as best illustrated in FIG. 2. This will allow pressures adjacent both the left atrium and the aortic arch to be sensed in a manner more fully set forth below. In addition, the sounds of the mitral valve MV and aortic valve AV can be picked up for processing without moving the catheter 20 once it is positioned.

The length of the distal balloon is desirably minimized so as to lie adjacent the left atrium over most of its length for good pressure coupling and so as to reduce any interference by the aorta or otherwise with its reception of the left atrial pressure waves. In accordance with these objectives, the overall length of the balloon 28.1 is selected to be preferably between about 1.5 and 3.5 cm, more preferably about 2.5 cm (with a taper at each end of perhaps about 0.25 cm). The overall length of the balloon 28.2 may suitably be about 3.6 cm (with a taper at each end of perhaps about 0.3 cm).

FIG. 7 illustrates to the left and right sides of the centerline 48 of an esophagus ES, the left atrial/aortic arch spatial relationships for a short female $P_{SF}$ (height of about 5'2") and for a tall male $P_{TM}$ (height of about 6'1").

These illustrated relationships are drawn to scale in a direction longitudinally of the esophagus. As illustrated in FIG. 7, the distance to the left atrium centerline 50 of the female $P_{SF}$ is at about 33 cm. along the catheter from the entrance to the nasal passage NP, while the distance to the left atrium centerline 52 in the male $P_{TM}$ is about 40 cm. from the entrance to the nasal passage. Thus, the distance to the left atrium in adults varies widely. However, as seen in FIG. 7, the distance between the left atrium LA and aortic arch AAR is substantially the same in both the tall man and the short woman. Furthermore, it is my belief as a medical doctor that this distance is substantially constant, as illustrated by FIG. 7, in virtually all adults. This substantially constant relationship allows the catheter to advantageously be provided in a single standardized size.

In order to provide a standardized catheter which will suitably fit substantially all adult patients so as to reduce the expense, inconvenience, and complexity inherent in carrying and using a set of catheters of various sizes, in accordance with the present invention, the upper balloon 28.2 is spaced away from the lower balloon 28.1 the distance set forth above so that when the lower balloon 28.1 is positioned adjacent the left atrium LA, the upper balloon 28.2 is suitably positioned adjacent the aortic arch AAR in either shorter adults, such as $P_{SF}$, or in taller adults, such as $P_{TM}$. It can be seen that with this spacing the upper balloon will not be so near the pulmonary artery PA as to receive interference from the pressure thereof. A greater distance between balloons or a greater length of the upper balloon 28.2 which would place it so high in the esophagus that a gag reflex may be initiated is not considered to be desirable.

My prior aforesaid patents disclose suitable positioning of a balloon beside the left atrium for receiving the pressure waves therefrom for suitably obtaining determinations of mean left atrial and mean left atrial transmural pressures. With the balloon thus suitably positioned, my prior aforesaid patents disclose suitably obtaining quantitative determinations, from the effects of left atrial pressure on the balloon, of mean left atrial and mean left atrial transmural pressures.

In accordance with the present invention, the balloons 28.1 and 28.2 are used along with blood pressure cuff 22 and the electrocardiogram, as needed, to noninvasively obtain the pressures and other information needed for suitably monitoring cardiac performance, i.e., systolic time intervals, an index of cardiac output, a measure of pulse wave velocity, left ventricular contractility index (dp/dt/MLAP), and pulse amplitude ratios before, during, and after performing the Valsalva maneuver. After the following discussion of an improvement in the obtaining of a determination of mean left atrial and mean left atrial transmural pressures, the use of the apparatus of the present invention for obtaining determinations of each of the above parameters of cardiac performance will in turn be discussed. The computer may be suitably programmed to implement these procedures, using principles commonly known to those of ordinary skill in the art to which this invention pertains.

Positioning of Catheter

As discussed in my prior patents, the distal balloon 28.1 must be correctly positioned adjacent the left atrium in order to suitably obtain the wave form for determining mean left atrial and mean left atrial transmural pressure. One suitable means of positioning the atrial balloon utilizes a bi-polar electrode (which comprises two spaced electrodes, illustrated at 51 in FIG. 7), which is attached to the catheter 20 just above the balloon 28.1, as disclosed in my U.S. Pat. No. 5,570,671. The bi-polar electrode leads, illustrated at 51a and 51b in FIG. 4, are preferably embedded in the material which forms the double lumen catheter in order to prevent their interference with pressure signals. As the electrode 51 is moved up the esophagus, its signals are used to obtain an electrogram at each of a series of incremental depths. The length of the negative portion of the largest absolute value of the P wave is determined for at least one P wave in each incremental electrogram. The depth to the center of the left atrium is selected to be that which corresponds to the incremental electrode depth at which the electrogram therefor shows the greatest negative portion length. The balloon 28.1 is then positioned at that selected depth for obtaining the cardiac performance information as hereinafter discussed.

While the above means for positioning the balloon 28.1 is considered to be very reliable, the bi-polar electrode adds additional cost to the catheter, and there is "wait" time at each increment of position until the electrogram readings "settle down." In order to eliminate the need for esophageal electrodes, as well as to provide an alternative means for balloon positioning, in accordance with the present invention, the balloon 28.1 may be alternately positioned, if desired, in accordance with the following procedure. With the balloon 28.1 in the stomach (not shown), it is inflated to a suitable pressure of perhaps 6 cm. water pressure. While thus pressurized, the catheter 20, which may be suitably marked at perhaps 1 cm. increments, is drawn up the esophagus starting at a suitable depth of perhaps about 48 cm (from tip of nose to center of balloon 28.1) which is known to be well below the position of the left atrium. Each of the depths is manually inputted to the controlling and information processing means 12.

Figure 8:
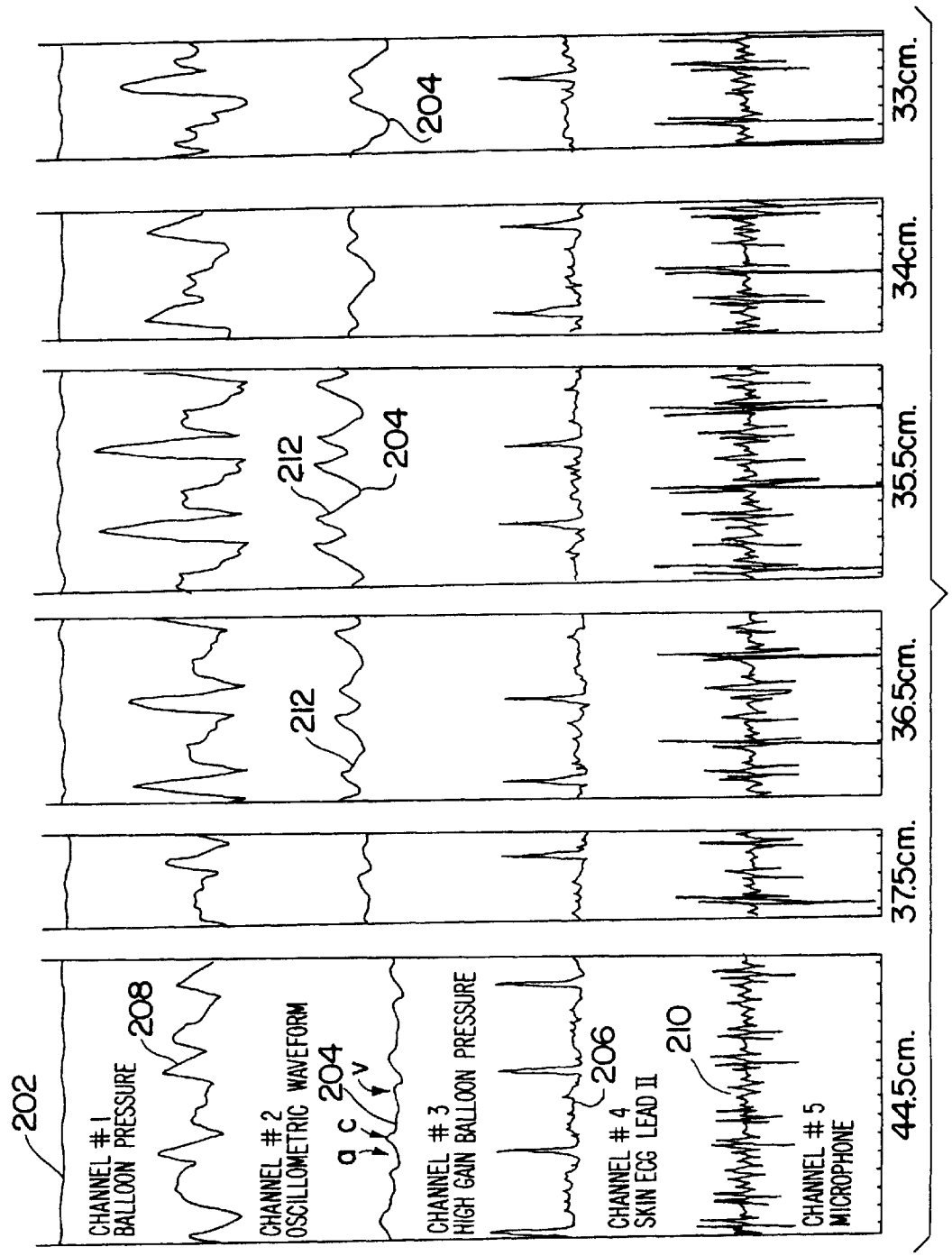
FIG. 8 is a graph of a series of simultaneous wave forms at various esophageal depths of a balloon in a relatively tall subject illustrating changes in the balloon pressure wave form for positioning of the balloon adjacent the left atrium.

With reference now to FIG. 8, a five channel graph is illustrated, with segments of the graph being produced at various balloon depths. Thus, the five channel tracing to the left of FIG. 8 shows tracing of balloon pressure at a catheter depth of 44.5 cm. FIG. 8 also shows tracings at depths of 37.5 cm, 36.5 cm, 35.5 cm, 34.0 cm and 33.0 cm.

These tracings are for the tall male PTM. With reference to FIG. 7, it can be seen that at a depth of 44.5 cm, the top of the balloon 28.1 is barely adjacent the bottom of the left atrium LA. However, it can be seen from pressure tracing 202, and more particularly the high gain tracing 204, that the balloon has been pulled up to such an extent that the pressure within the balloon is being influenced by the filling and emptying of the left atrium. This is also shown by the oscillometric waveform 208. All of these tracings are based on signals sent to the controlling and processing means 12 by the transducer 36.1, the means 12 causing these waveforms to be transmitted to the monitor 14 and the recorder 16. The means 12 also receives inputs from the ECG leads 18.1 and 18.2 (lead II), and from the microphone 34.1, (as well as from other inputs), and tracings representative of these signals are shown at 206 and 210, respectively.

While tracings produced by recorder 16 may be used, it is envisioned that most health care professionals will use the monitor 14 to position the catheter. The monitor 14 may, for example, display the balloon pressure 204, depth of distal balloon, oscillometric wave form 208, and simultaneous ECG wave 206 for perhaps the three most recent distal balloon depths so that the balloon pressure waves 204 at these depths may be compared.

Figure 9:
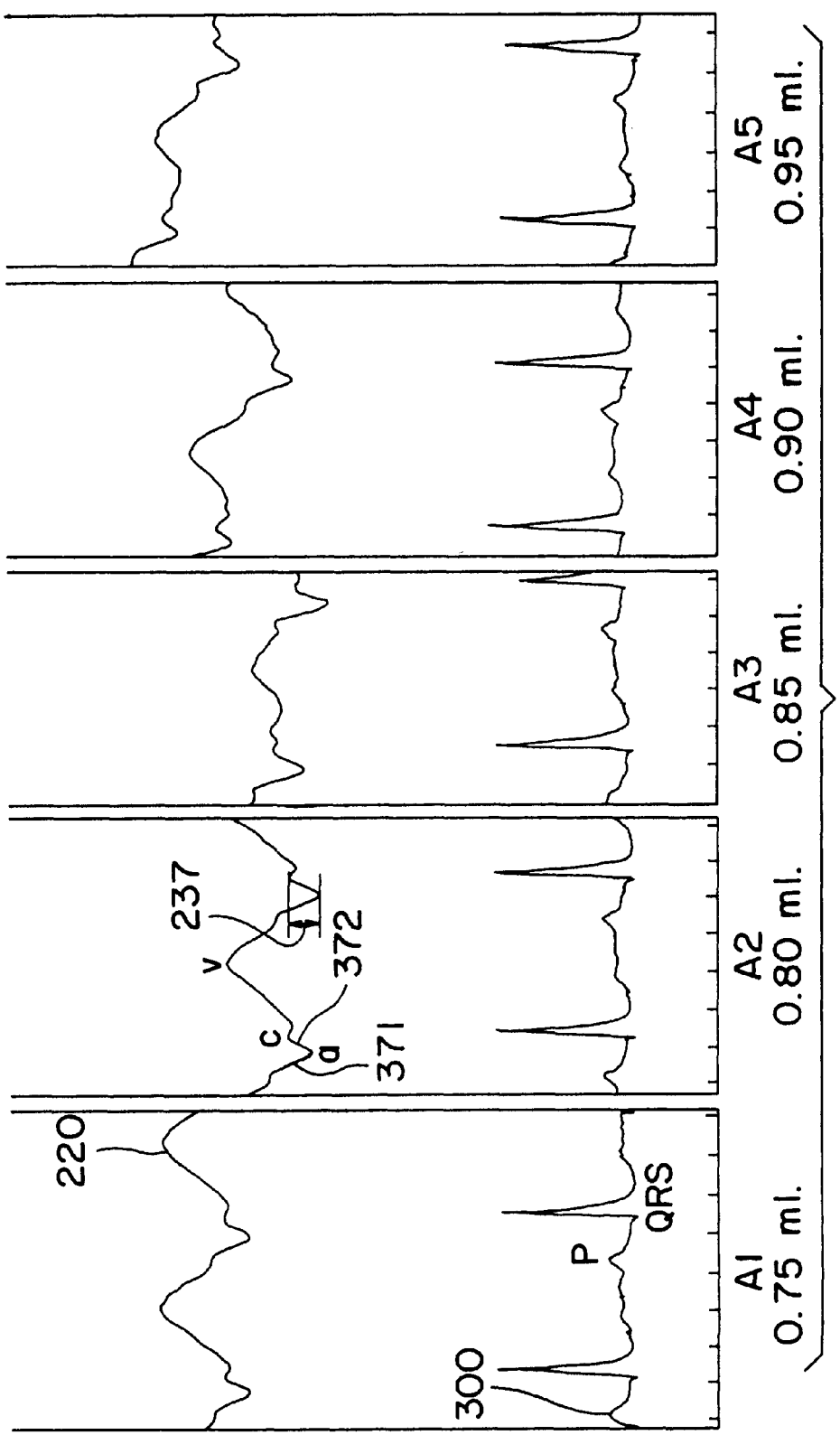
FIG. 9 is a graph illustrating a series of consecutive left atrial balloon pressure waves at various balloon inflation volumes and simultaneous ECGs illustrating an improved method of obtaining a quantitative determination of mean left atrial pressure.
Figure 14:
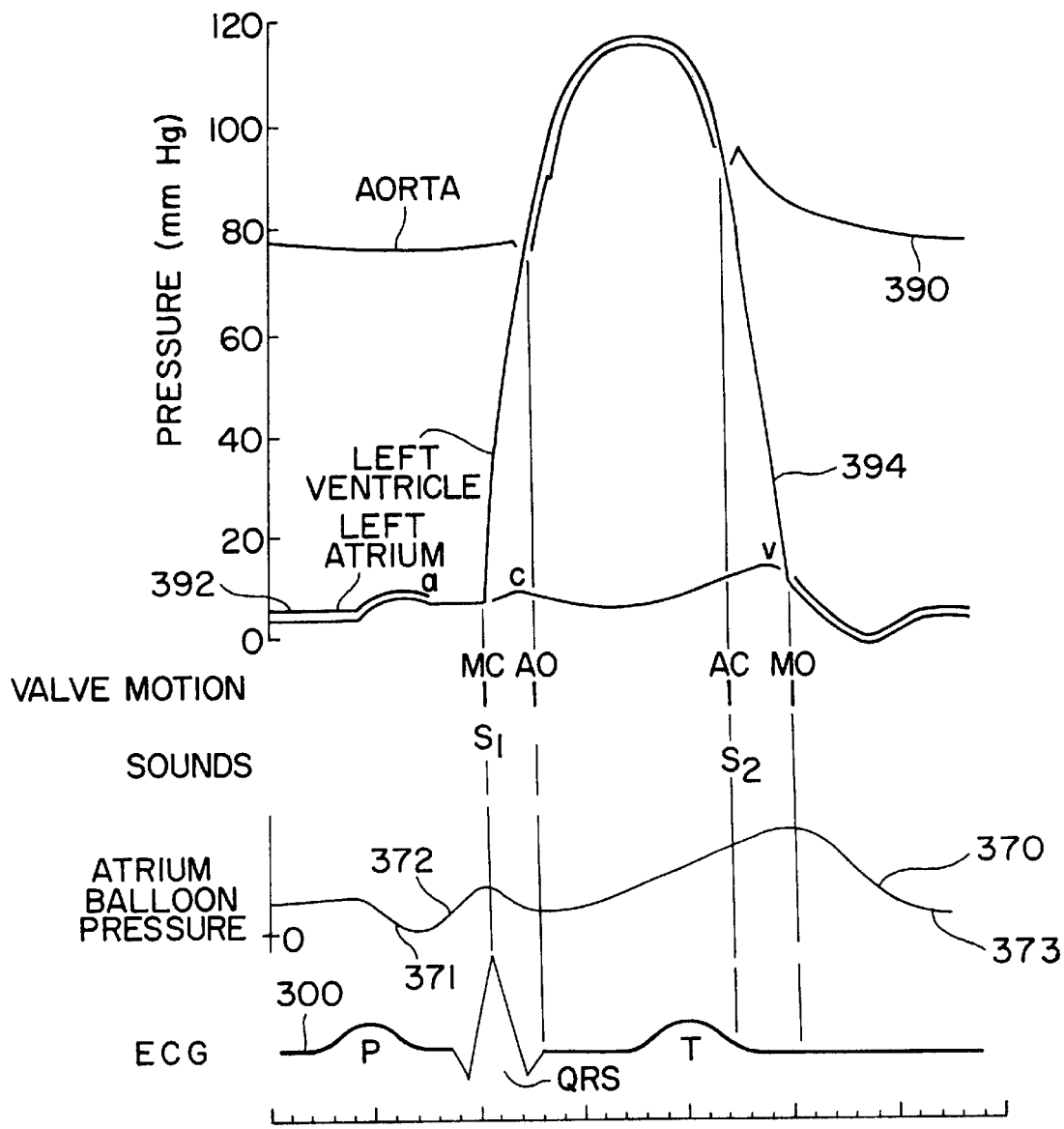
FIG. 14 is a graph of an idealized left atrial balloon pressure wave form and simultaneous ECG and its relation to various heart wave forms for use in describing the obtaining of an index of cardiac output.

As seen in FIG. 8, the tracing 204 of high gain raw balloon pressure shows a modified a, c, v wave form at balloon depths of 44.5 and 37.5 cm. (The balloon pressure wave form is referred to gas a modified a, c, v wave form because the "a" peak of the balloon wave form is inverted from the "a" peak of the a, c, v wave form, illustrated at 392 in FIG. 14, of pressures taken from within the left atrium. This wave form is not unusual in some patients. Both troughs and peaks in the wave form, which are points where the slope of the wave form changes between positive and negative and which are indicated in FIGS. 8, 9, and 14 by "a", "c", and "v", are referred to herein as "peaks". The wave portions which contain these "a", "c", and "v" peaks are referred to as "a", "c", and "v" waves, respectively. FIG. 9 illustrates an externally derived pressure measurement technique which may not work in all persons. The a, c, v wave form extends generally between points 371 and 373 on the idealized atrial balloon pressure curve 370 of FIG. 14.

I have now determined that there is a depth in the esophagus at which there is a major change in the balloon pressure wave form 204 so that the left atrial pressure (a, c, v) wave form is no longer apparent. Moreover, the amplitude of the wave form at this depth has abruptly substantially increased, further indicating that the balloon pressure is being affected by a different pressure source within the body. It is believed that the new wave form, illustrated at 212, at the higher depths (36.5 cm and 35.5 cm in FIG. 8) may be a wave form caused by the pulmonary artery PA. More importantly, the characteristic left atrial pressure wave form with its much smaller amplitude is no longer apparent at the 36.5 cm depth, indicating that the balloon 28.1 has moved beyond the position of the left atrium. In accordance with the present invention, the balloon 28.1 is thus positioned at a catheter depth slightly below the uppermost depth (36.5 cm in FIG. 8) at which the characteristic left atrial pressure wave (a, c, v) first disappeared. Taking into consideration the size of the left atrium, it is considered preferred that the balloon 28.1 be lowered from this depth (36.5 cm) perhaps about 2 to 3 cm (to a depth of perhaps about 39 cm in this subject) until a good left atrial pressure wave form is seen, and the monitor 14 may be used as an aid in such positioning. The catheter 20 may then be secured to the nose or lip, and the various measures of cardiac performance described hereinafter obtained with the distal balloon 28.1 in position adjacent the left atrium and the proximal balloon 28.2 confidently in position adjacent the aortic arch.

The left atrial pressure signal may be subjected to fast Fourier transform analysis, in accordance with principles commonly known to those of ordinary skill in the art to which this invention pertains, to correct each frequency component for amplitude and phase shift using a suitable regression equation for the catheter, including a factor for barometric pressure. The true left atrial pressure signal is reconstructed by adding all corrected frequencies, and the correct timing of the wave form reestablished with the ECG.

While positioning of the balloon 28.1 has been described, it should be appreciated that the balloon 28.2, which is maintained in the same spatial relationship to the balloon 28.1, will accordingly be positioned as shown in FIG. 7. Also, while the distances used are for the tall male $P_{TM}$, the same positioning technique would be used for other persons.

Thus, as can be seen from FIG. 7, the balloon 28.1 would be moved down for person $P_{SF}$ 2–3 cm after the waveform 212 had been detected.

The aortic balloon 28.2 may alternatively be positioned, after placing it deep in the esophagus and suitably inflating it to, for example, 6 cm of water, bringing the balloon 28.2 slowly up the esophagus such as in 1 cm increments and looking for the typical aortic pressure signal, which will be inverted, for reasons discussed hereinafter, using the ECG for timing. Other suitable means may of course be used for positioning the left atrial and/or aortic balloons.

Determining Mean Left Atrial Pressure and Mean Left Atrial Transmural Pressure My prior aforesaid patents disclose methods using the oscillometric principle for determining quantitatively mean left atrial and mean left atrial transmural pressures. In accordance with these methods, pressure in a balloon adjacent the left atrium is gradually raised, and the balloon pressure, at peak amplitude of the balloon pressure oscillations (or the peak amplitude of sound waves passing through the inflated balloon) effected by the pressure outside the balloon is noted. In accordance with the oscillometric principle, this balloon pressure is equal to the mean pressure outside the balloon which is acting on it. In other words, when the wall of the left atrium is unloaded such that the mean transmural pressure gradient is zero, the transmission of pressure changes is optimal and is not influenced by compliance of the atrial wall.

It is however believed that the balloon 28.1 may (in some patients) pick up aortic pressure waves (from the descending aorta) which may combine with the left atrial pressure waves and thus skew the results. It is also believed that this effect is predominant during the period of time between the "c" and "v" atrial wave peaks when rapid changes in aortic pressure are occurring and that this effect is insubstantial during the period of time of the "a" wave portion (which includes wave portions 371 and 372 of the atrial wave form, or between the P wave and the peak of the QRS complex on the ECG, when aortic pressure 390 tends to be relatively constant (as is illustrated in FIG. 14). Therefore, with reference now to the pressure wave of balloon 28.1, as shown at 220 in FIG. 9, in order to more precisely obtain a determination of mean left atrial and mean left atrial transmural pressures, at least in some patients, in accordance with the present invention, the balloon pressure during the "a" wave portion is used (instead of the entire wave form) for determination thereof, as discussed hereinafter.

With the catheter 20 in position, the proximal (aortic) balloon 28.2 is evacuated to perhaps about −20 mm Hg after which perhaps about 0.5 ml of air is added. This balloon 28.2 is connected to the transducer 36.2 to measure esophageal pressure continuously. The distal (atrial) balloon 28.1 is evacuated to perhaps about −20 mm Hg then filled at a rate of perhaps about 0.01 ml free air per second.

FIG. 9 shows representative segments A1 to A5 of a series of five graphs or balloon pressure tracings of the actual left atrial pressure waveform 220, amplified by a 10-fold increase in gain and having a simultaneous ECG 300 for timing, in the tall male in a supine position with the balloon pressure steadily increased by adding air in increments of 0.05 ml to the balloon. Thus, the wave form 220 in segments A1 to A5 are with the balloon pressure increased to have balloon volumes of 0.75 ml, 0.80 ml, 0.85 ml, 0.90 ml, and 0.95 ml of air respectively.

Using the ECG 300 for timing, the "a" wave portion, which is part of the entire left atrial pressure wave 220, is identified and the peak to peak voltage, illustrated at 237, of the "a" wave portion 371 or 372 having the highest voltage (highest amplitude) is measured at each of the balloon volumes A1 to A5 and stored in computer memory. This peak to peak voltage 237 is a measure of the "a" wave amplitude and represents the maximum voltage difference recorded from the atrial wave form during the time period from the P wave to the peak of the QRS complex on the ECG.

The signals are subjected to fast Fourier transform analysis, in accordance with principles commonly known to those of ordinary skill in the art to which this invention pertains, to correct each frequency component for amplitude and phase shift using a suitable regression equation for the catheter. The true left atrial pressure signal is then reconstructed by adding all corrected frequencies and the correct timing of the wave form re-established with the ECG.

When the left atrial balloon filling cycle is completed, the recordations of the balloon pressure at preferably end-expiration are examined, such as by use of a suitably programmed computer, and the time when one or more, such as 5, contiguous "a" wave portions at a certain balloon volume reached the highest recorded voltages, corresponding to peak oscillation pressure, is identified. The balloon pressures for determining mean left atrial and mean left atrial transmural pressures should be taken at the same point in the respiratory cycle, which is preferably end-expiration. The pressure in atrial balloon 28.1 at that time is identified and displayed on the screen.

Alternatively or additionally, the heart sounds passing through the inflated balloon 28.1 are recorded by pressure compensated microphone 34.1 and suitably digitized, as discussed more fully in my aforesaid U.S. Pat. No. 5,570,671. The mean balloon pressure at preferably end-expiration at the sound wave peak amplitude is suitably inputted to the computer and displayed on the monitor, and the mean left atrial and mean left atrial transmural pressures are determined therefrom and displayed as discussed herein for balloon pressure oscillations.

As discussed in my prior patents, there is an abrupt slope change from a fast to a slowed rate of pressure increase indicative of the equalization of balloon pressure with the surrounding tissue pressure prior to balloon expansion. This slope change pressure is determined from the atrial balloon pressure-volume curve and inputted to the computer. In order to determine mean left atrial transmural pressure, the pressure (preferably end-expiratory pressure) at this slope change is subtracted from preferably end-expiratory pressure at the balloon oscillation peak, and this pressure may then be displayed by the monitor.

Figure 17:
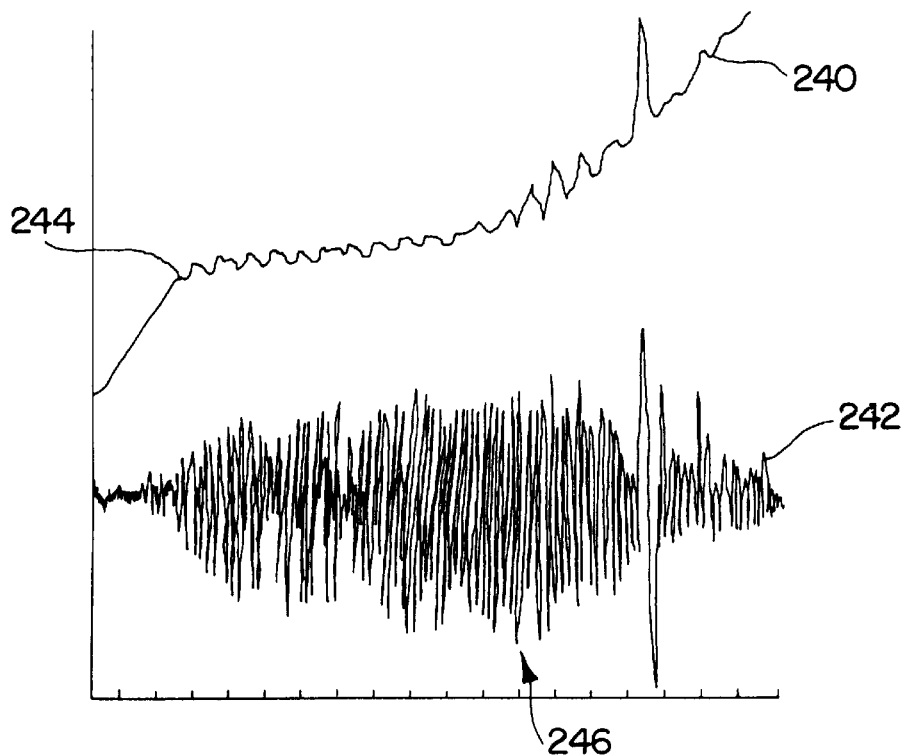
FIG. 17 is a graph or tracing of atrial balloon pressure and the simultaneous differentiated atrial wave form.

Referring to FIG. 17, there is illustrated at 240 a graph or tracing of pressure in the atrial balloon while adjacent the left atrium and at 242 a simultaneous graph or tracing of balloon pressure oscillations. Tracings 240 and 242 are similar to those of FIGS. 9 and 11 respectively of my aforesaid U.S. Pat. No. 5,263,485, except as hereinafter discussed. The abrupt slope change indicative of the equalization of balloon pressure with the surrounding tissue pressure prior to balloon expansion is shown at 244. The signal for tracing 242 has been differentiated by use of a conventional analog or digital differentiator. As the signal peaks, the rate of voltage change increases, which is displayed by the differentiator. Advantageously, it is not necessary to filter out low frequencies with this technique. As seen in FIG. 17, the differentiated signal allows one to more clearly see the point of oscillation peak 246 so that mean left atrial and mean left atrial transmural pressures may be more precisely determined.

From the proximal (aortic) balloon 28.2, the esophageal end-expiratory pressure is obtained and inputted to the computer. In order to determine mean left atrial pressure, the esophageal end-expiratory pressure is added to the mean left atrial transmural pressure, and this pressure may also be displayed by the computer.

It was seen in the wave form segments A1 to A5 of FIG. 9 that the peak amplitude 237 of the "a" wave portion 222 occurred at a balloon volume of 0.85 ml (segment A3), which corresponds to a peak oscillation pressure of 16 cm water, which corresponds to a mean left atrial pressure of about 9.5 to 10 mm Hg, which is considered to be a normal value.

The measurement cycle may be repeated at a preset sampling frequency, and the information printed out and used as needed and for the determination of other cardiac performance parameters as discussed hereinafter.

A preferred method for determining mean left atrial pressure in accordance with the above discussion is illustrated generally at 650 in the flow chart of FIG. 22.

Determining Systolic Time Interval and Components Thereof

The systolic time interval ($QS_2$) comprises the duration of time from the beginning of the Q wave on the electrocardiogram to the time of the second heart sound $S_2$, which is in this case the sound of the aortic valve closing. During this time interval there are the two components or phases of left ventricular systolic activity, i.e., the pre-ejection period (PEP) and the left ventricular ejection time (LVET). PEP refers to the time spent by the ventricle increasing pressure on the volume of blood in it before ejection of the blood into the aorta, and LVET is the duration of the ejection phase. These time interval components may be used in various combinations to gauge ventricular performance. For example, a long PEP indicates that the heart is pumping against increased resistance, and the ratio PEP/LVET is known to decrease as cardiac output increases.

Figure 10:
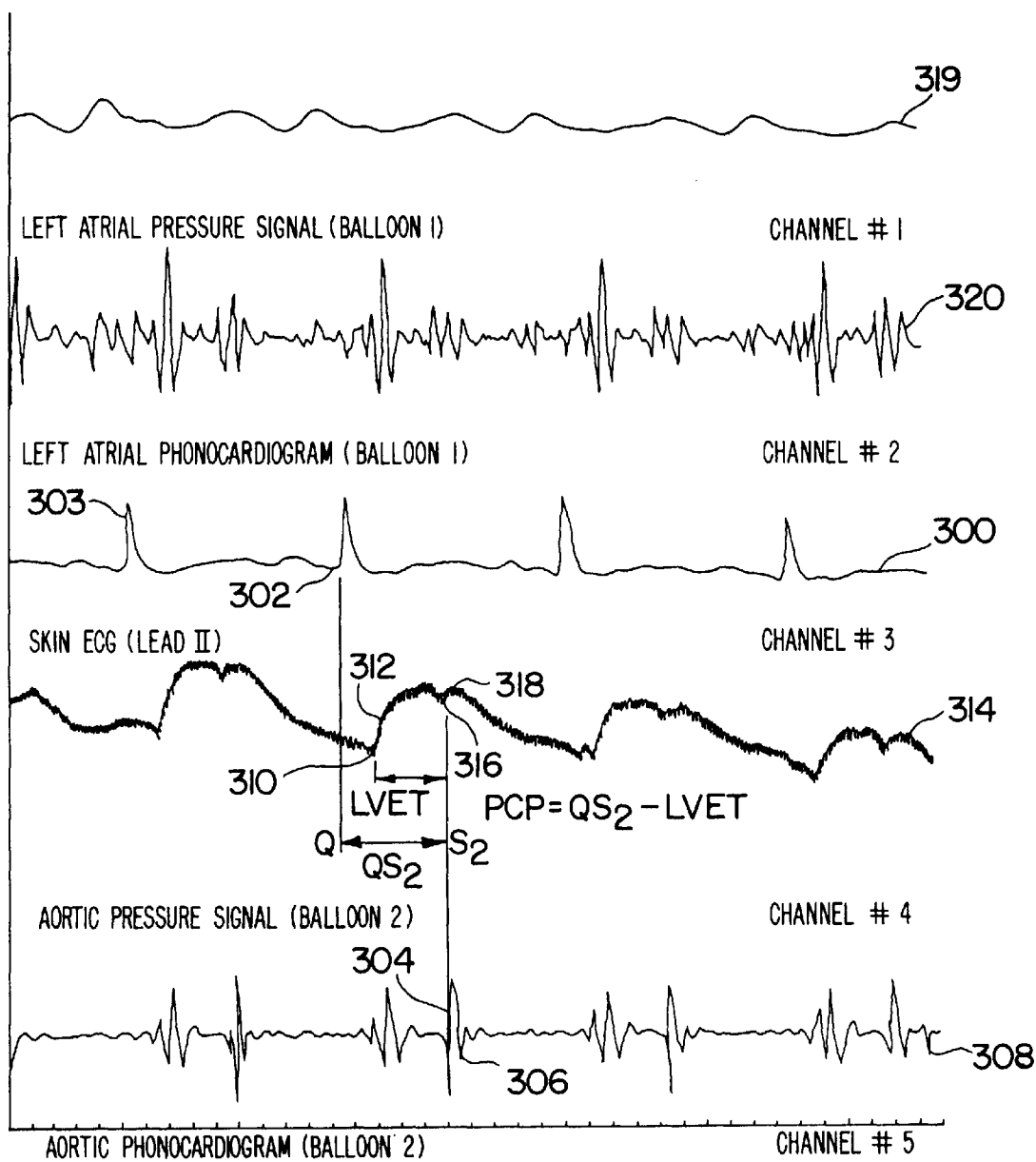
FIG. 10 is a graph of a series of simultaneous wave forms of the left atrial and aortic balloons and ECG illustrating the obtaining of systolic time intervals.

In order to reliably, conveniently, inexpensively, and continuously obtain systolic time intervals and components thereof, in accordance with the present invention, the catheter 20 and the ECG 18 are used preferably in combination, the catheter being provided with a pressure compensated microphone 34.2 with a 100 Hz high pass filter to create an aortic phonocardiograph. Thus, after the catheter is suitably positioned, as hereinbefore discussed, and the aortic balloon 28.2 is suitably inflated to a minimal pressure of perhaps about 2 to 4 mm Hg, the aortic pressure wave form from balloon 28.2, illustrated at 314 in FIG. 10, is suitably recorded and digitized, using the ECG for timing. The phonocardiogram, illustrated at 308, is also suitably recorded. The aortic wave form is desirably analyzed with fast Fourier transform analysis to correct phase shift and frequency components found using suitable equations for the catheter dimensions, and the aortic wave form is then reconstructed by adding the corrected frequency components.

The exemplary aortic pressure signal 314 shown in FIG. was taken with the subject sitting up. When a subject is lying flat, this signal may be inverted due perhaps to the aortic arch moving apart during systole. If the signal is inverted, it should desirably be re-verted electronically to show pressure increases during ventricular ejection.

Referring to FIG. 10, the time of onset Q (302) is obtained from the ECG, illustrated at 300, the QRS complex being shown at 303. The ECG is taken from lead II of the skin ECG. The time of $S_2$ is taken as the time of beginning, illustrated at 304, of the second heart sound, illustrated at 306, from the aortic phonocardiogram 308. The length of time of the total systolic time interval $QS_2$ is the time interval between times 304 and 302.

The beginning of LVET is taken as the time of beginning, illustrated at 310, of the upslope, illustrated at 312, of the aortic pressure signal, illustrated at 314, which indicates that the left ventricle has begun discharging blood into the aorta. The aortic pressure signal wave form 314 is taken from the balloon 28.2 adjacent the aortic arch.

The end of LVET is taken as the time, illustrated at 316, of the dicrotic notch, illustrated at 318, of the aortic wave form 314. The difference between times 316 and 310 is the LVET. If the dicrotic notch is badly distorted because of aortic valve pathology, LVET determination may have to be aborted.

PEP is the difference between $QS_2$ and LVET. However, PEP is still obtainable even if LVET cannot be obtained, as being the difference between times 310 and 302. Thus, while the use of the aortic phonocardiogram is preferred, this is an alternative way of obtaining a determination of PEP whereby at least one and perhaps both phases of the systolic time interval may be determined without the use of a phonocardiogram at all.

If desired for the purpose of determining PEP, the time 310 of beginning of upslope 312 of aortic pressure wave 314 may be suitably corrected for the time delay due to the distance from the aortic valve to the aortic balloon (the correction should be approximated by a constant and short time delay), using principles commonly known to those of ordinary skill in the art to which this invention pertains. However, I believe that the uncorrected time 310 may be normally sufficiently precise for determination of PEP as well as LVET.

FIG. 10 also shows at 319 and 320, respectively, the simultaneous left atrial pressure signal and the unfiltered left atrial phonocardiogram from the distal (atrial) balloon 28.1.

The PEP is suitably corrected for heart rate (PEP+0.4 HR), the LVET is suitably corrected for heart rate and sex (LVET+1.7 HR for men, LVET+1.6 HR for women), and the $QS_2$ is suitably corrected for heart rate and sex ($QS_2$+2.1 HR for men, $QS_2$+2.0 HR for women). For beat by beat analysis, these determinations may be meaned for perhaps 10 beats and may be suitably displayed.

Figure 11:
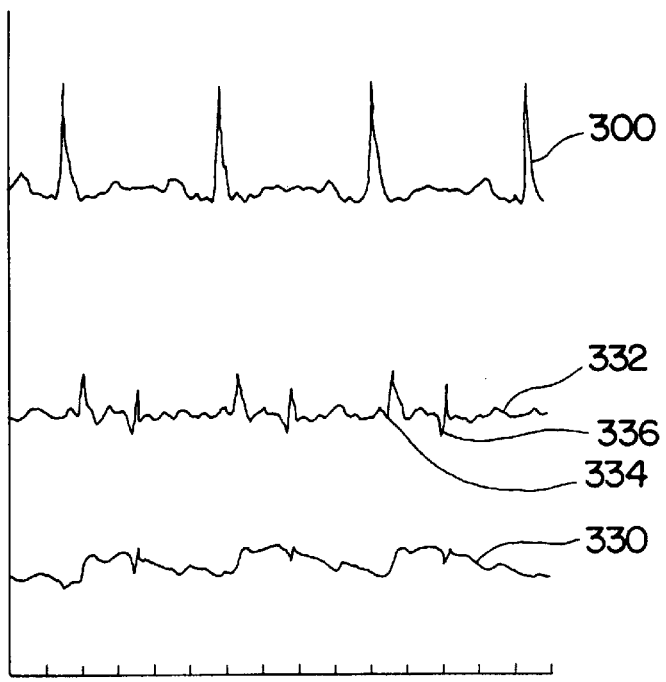
FIG. 11 is a graph of a series of simultaneous wave forms of the aortic balloon and ECG illustrating an alternative method of obtaining systolic time intervals.

Referring to FIG. 11, there is illustrated an alternative procedure for determining LVET. Using the simultaneous ECG 300 for timing, a raw aortic pressure signal (with the proximal balloon 28.2 inflated to a volume of perhaps about 0.7 ml air) is illustrated at 330, and this signal is suitably differentiated to obtain differentiated aortic signal 332. The sharp upsiope beginning at point 334, which occurs at the end of the QRS wave, is believed to signal the beginning of LVET. The point 336 is believed to signal the end of LVET because of aortic valve closure (illustrated at AC in FIG. 14) at this point. Thus, LVET, in accordance with this alternative embodiment of the invention, is believed to be the duration of time between points 334 and 336.

A preferred method for determining systolic time intervals and components thereof in accordance with the above discussion is illustrated generally at 660 in the flow chart of FIG. 23.

The ratio PEP/LVET is considered to be a useful index of ventricular performance, with a minimum value indicating optimum performance.

Determination of Pulse Amplitude Ratios During Valsalva Maneuver

The Valsalva maneuver involves having a patient create and maintain an airway pressure with open glottis by blowing into a mouthpiece to pressurize a mercury column to 40 mm Hg. (or, if the patient cannot generate this pressure, perhaps 20 to 25 mm Hg.) and holding it there for 10 seconds. By examining the arterial blood pressure during and immediately after this maneuver, a diagnosis of heart failure may be made since a normal heart and a heart in hypertensive heart failure respond to the maneuver in different ways, as discussed in "Effects of Valsalva's Maneuver on the Normal and Failing Circulation" by E. P. Sharpey-Schafer, *British Medical J.*, Mar. 19, 1955, p. 693 to 695. A healthy heart shows an increase in pulse pressure then damping of the pressure during the Valsalva maneuver, followed by a dramatic increase in pulse pressure and decrease in heart rate with rapid damping of the pulse pressure when the Valsalva maneuver is released. A diseased heart does not respond in this fashion.

In accordance with the present invention, the catheter 20 is used to conveniently and reliably provide a wave form of (1) left atrial pressure by use of the distal (atrial) balloon 28.1 similarly as previously discussed and/or (2) aortic pressure by means of proximal (aortic) balloon 28.2 (while inflated to perhaps about 6 mm Hg) as previously discussed. Each of these wave forms will show the characteristics of a normal or failed heart, as the case may be, during and immediately after the Valsalva maneuver is performed.

Instead of being connected to a mercury column, the mouthpiece may instead be connected to a precalibrated transducer and feedback of airway pressure provided to guide the patient. Alternatively, esophageal pressure can be used to demonstrate the Valsalva maneuver without recourse to airway pressure by using the atrial or aortic balloons. The patient should be sitting in an upright position in order for esophageal pressure measurements to be provided by the atrial or aortic balloon, which is evacuated to perhaps about −20 mm Hg., then filled with perhaps about 0.4 ml air for this purpose.

Figure 12:
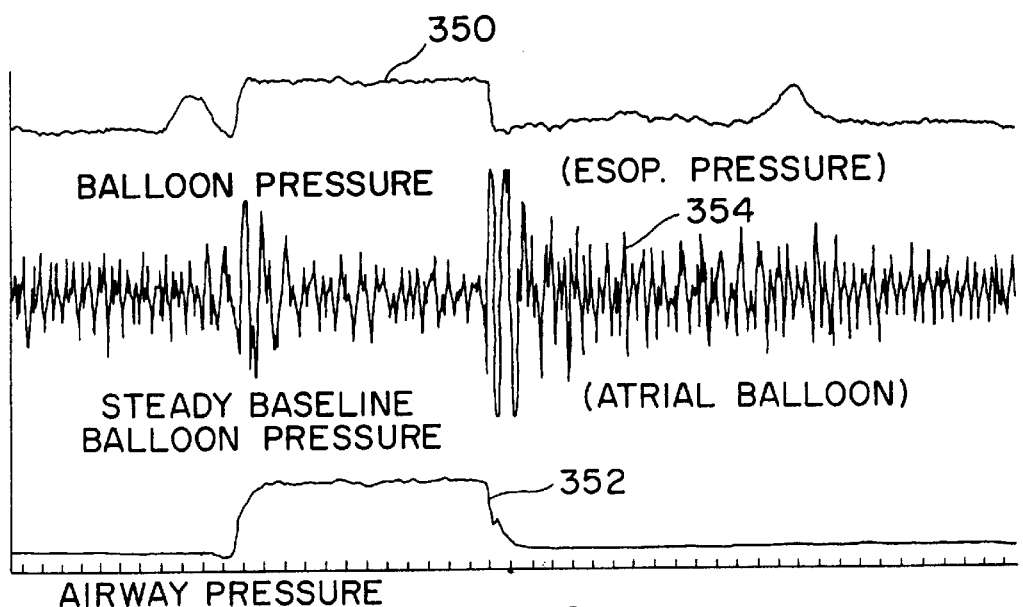
FIGS. 12 and 13 are each graphs of a series of simultaneous wave forms of the left atrial and aortic balloons and airway pressure illustrating respective alternative ways of obtaining pulse amplitude ratios while performing the Valsalva maneuver.

FIG. 12 illustrates one method of measuring pulse amplitude ratios following the Valsalva maneuver.

Illustrated at 350 is an increase in esophageal pressure (about 30 cm water) as determined by the aortic balloon for a period of time (about 10 seconds) as the Valsalva maneuver is being performed by an upright subject. This is confirmed by simultaneous increased airway pressure (about 40 cm water), illustrated at 352, for the same period of time. Immediately after performance of the Valsalva maneuver, the left atrial balloon wave form, illustrated at 354, shows a dramatic increase in left atrial pressure, and a decrease in heart rate, characteristic of a normal heart. In order that the pulse amplitude pattern of the left atrial balloon pressure may be easy to view and work with, in accordance with the present invention, the left atrial pressure oscillometric wave form 354 is preferably placed on a steady baseline, in accordance with procedures discussed in my aforesaid patents and using principles commonly known to those of ordinary skill in the art to which this invention pertains.

Figure 13:
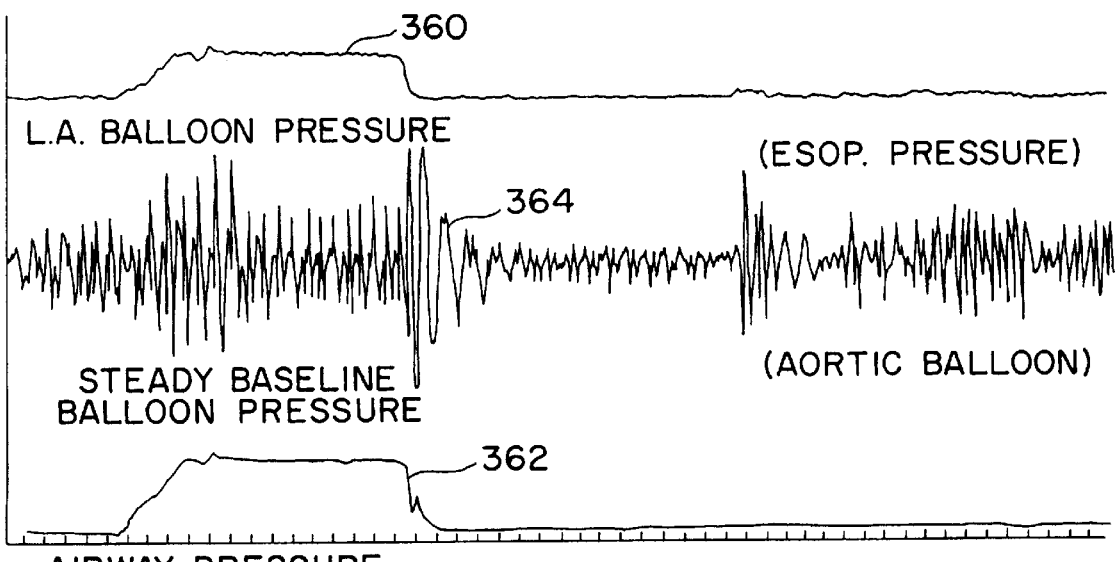

FIG. 13 illustrates an alternative method of measuring pulse amplitude ratios following the Valsalva maneuver. Illustrated at 360 is an increase in esophageal pressure (about 30 cm water) as determined by the left atrial balloon for a period of time (about 10 seconds) as the Valsalva maneuver is being performed by an upright subject. This is confirmed by simultaneous increased airway pressure (about 40 cm water), illustrated at 362, for the same period of time. (Airway pressure is measured by a transducer associated with the mouthpiece.) Immediately after performance of the Valsalva maneuver, the pressure, illustrated at 364, in the proximal or aortic balloon 28.2 shows a pulse amplitude pattern of aortic pressure characteristic of a normal heart. In order that the pulse amplitude pattern of the aortic balloon pressure may be easy to view and work with, the aortic balloon pressure wave form 364 is also preferably placed on a steady baseline.

Figure 24A:
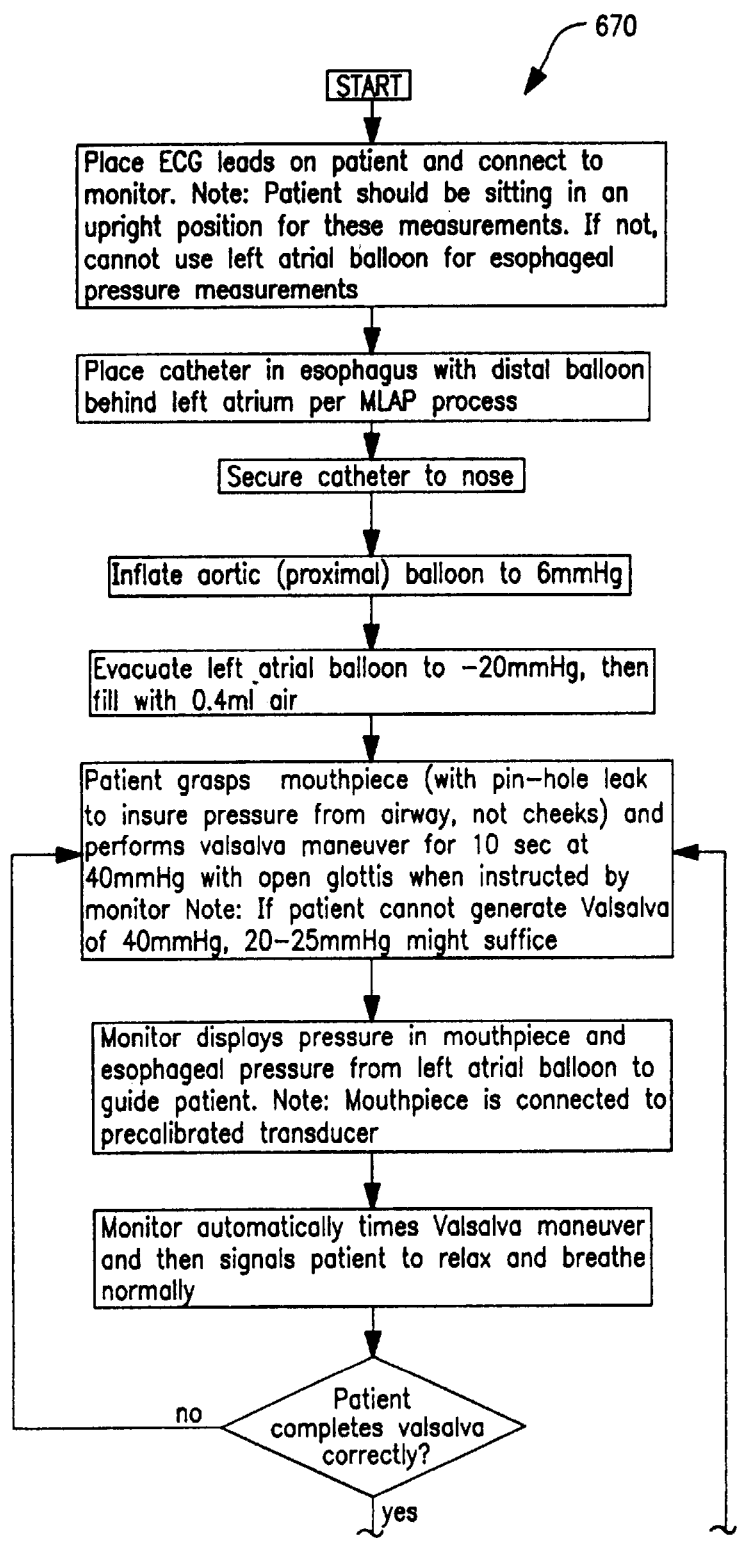
FIG. 24 is a flow chart of a preferred method of determining pulse amplitude ratios during the Valsalva maneuver.
Figure 24B:
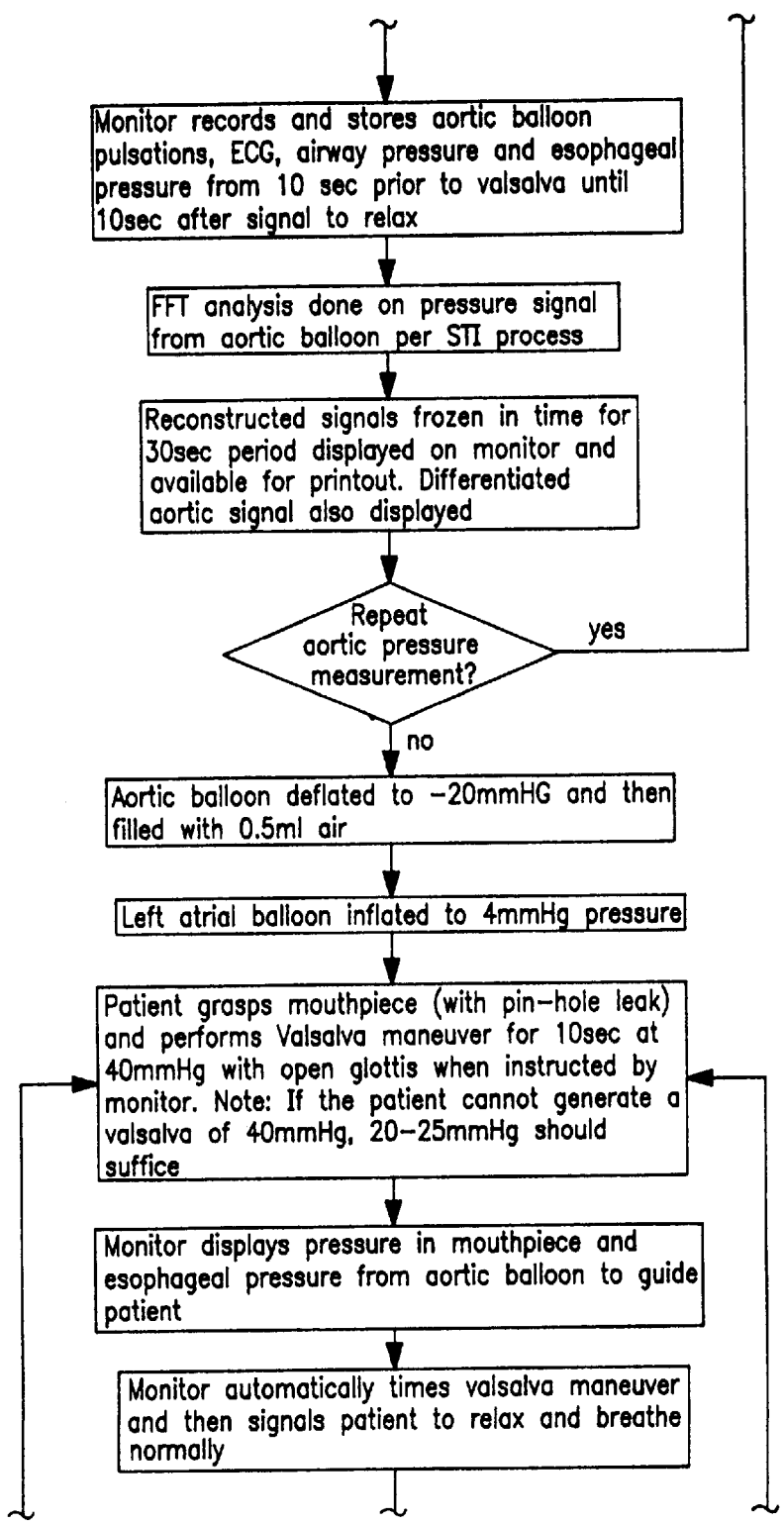
Figure 24C:
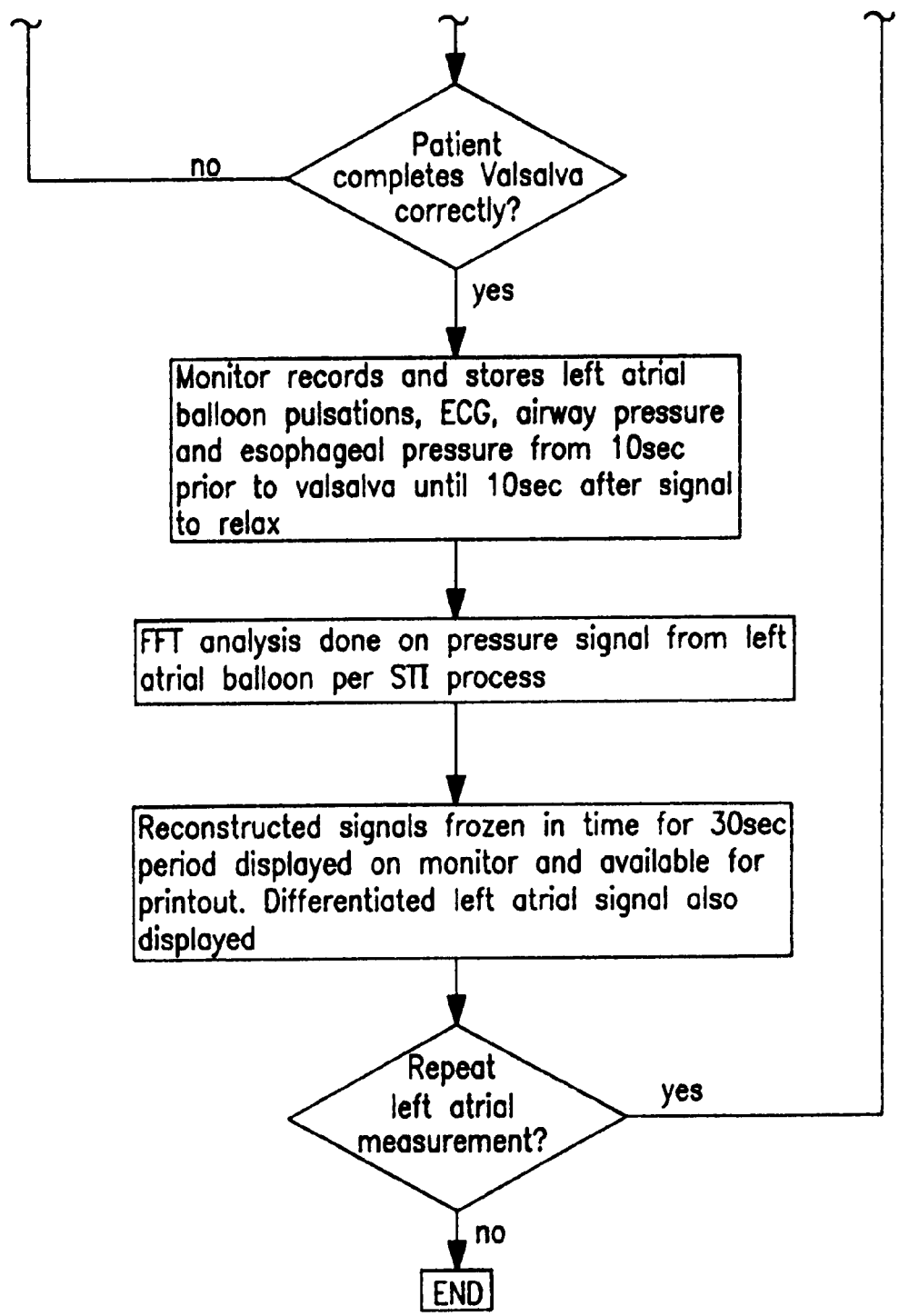

A preferred method for determining pulse amplitude ratios during the Valsalva maneuver in accordance with the above discussion is illustrated generally at 670 in the flow chart of FIG. 24.

Determination of Index of Cardiac Output

In FIG. 14, the pressure in the left atrial balloon 28.1, which has been filled with a gas in accordance with the oscillometric principle set forth above, is illustrated ideally by line 370. FIG. 14 also ideally illustrates, for purposes of relating the timing of various heart events with the atrial balloon pressure line 370, aortic, left atrial, and left ventricle pressures, illustrated at 390, 392, and 394 respectively, and the times of closing MC of mitral valve MV, opening AO of aortic valve AV, closing AC of aortic valve AV, and opening MO of mitral valve MV. The first and second heart sounds are indicated as occurring at times $S_1$ and $S_2$ respectively.

In accordance with the present invention, an index of cardiac output is obtained which is based on my belief that the ""a" wave portion (caused by left atrial contraction), the "c" wave portion thereof (caused by left ventricular contraction), and the "v" wave portion thereof (caused by pulmonary venous return to the left atrium) of the balloon-sensed left atrial wave form 370 will each increase or decrease in proportion to an increase or decrease in cardiac output, each wave reflecting a different manifestation of cardiac activity. In order to accomplish this, the area under the left atrial balloon pressure curve 370 during a heart beat may be integrated to obtain an index of cardiac output. In order to do so efficiently, the ECG electrodes 18.1 and 18.2 are connected to the surfaces of the skin of the person P and the catheter 20 is properly positioned with the left atrial balloon 28.1 behind the left atrium (or below if the person P is supine). The left atrial balloon 28.1 is then suitably pressurized, as previously discussed, to peak oscillation pressure (to unload the left atrial wall, the transmural pressure being at this time zero) and is then held at that pressure. As previously discussed, in accordance with the oscillometric principle, when the balloon pressure is at peak oscillation pressure, this balloon pressure is equal to the mean pressure outside the balloon which is acting on it so that the wall of the left atrium is unloaded (the mean transmural pressure gradient is zero). The transmission of left atrial pressure changes is, during this unloaded state, optimal and is not influenced by compliance of the atrial wall. Both the ECG and a phonocardiogram from the left atrial balloon are displayed on the CRT monitor 14 in real time. The health care personnel will evaluate the wave forms being displayed and make a judgement as to whether or not the mitral valve is damaged, which may invalidate the measurements due to back flow of blood from the left atrium.

Figure 25A:
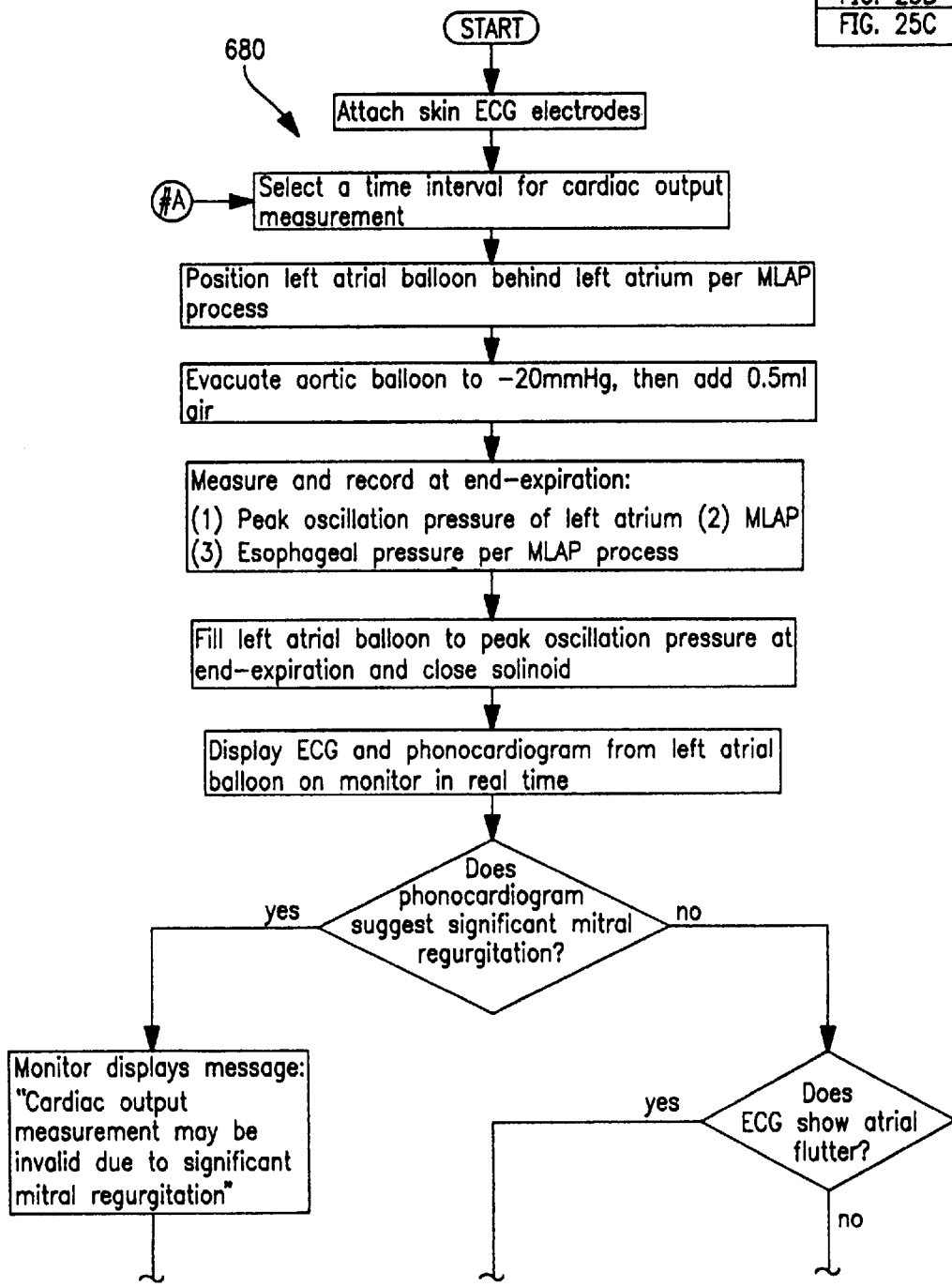
FIG. 25 is a flow chart of a preferred method of determining an index of cardiac output using the left atrial balloon.
Figure 25B:
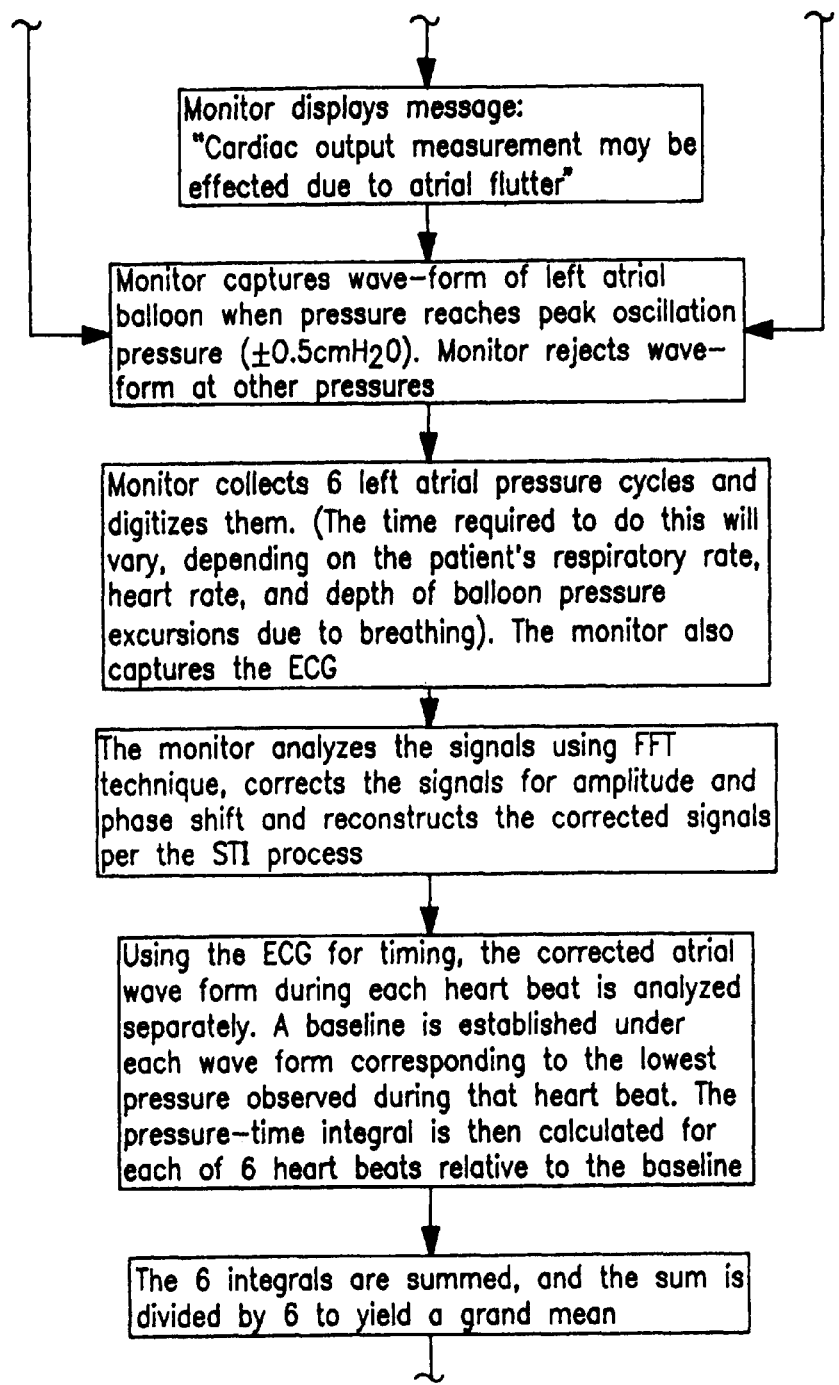
Figure 25C:
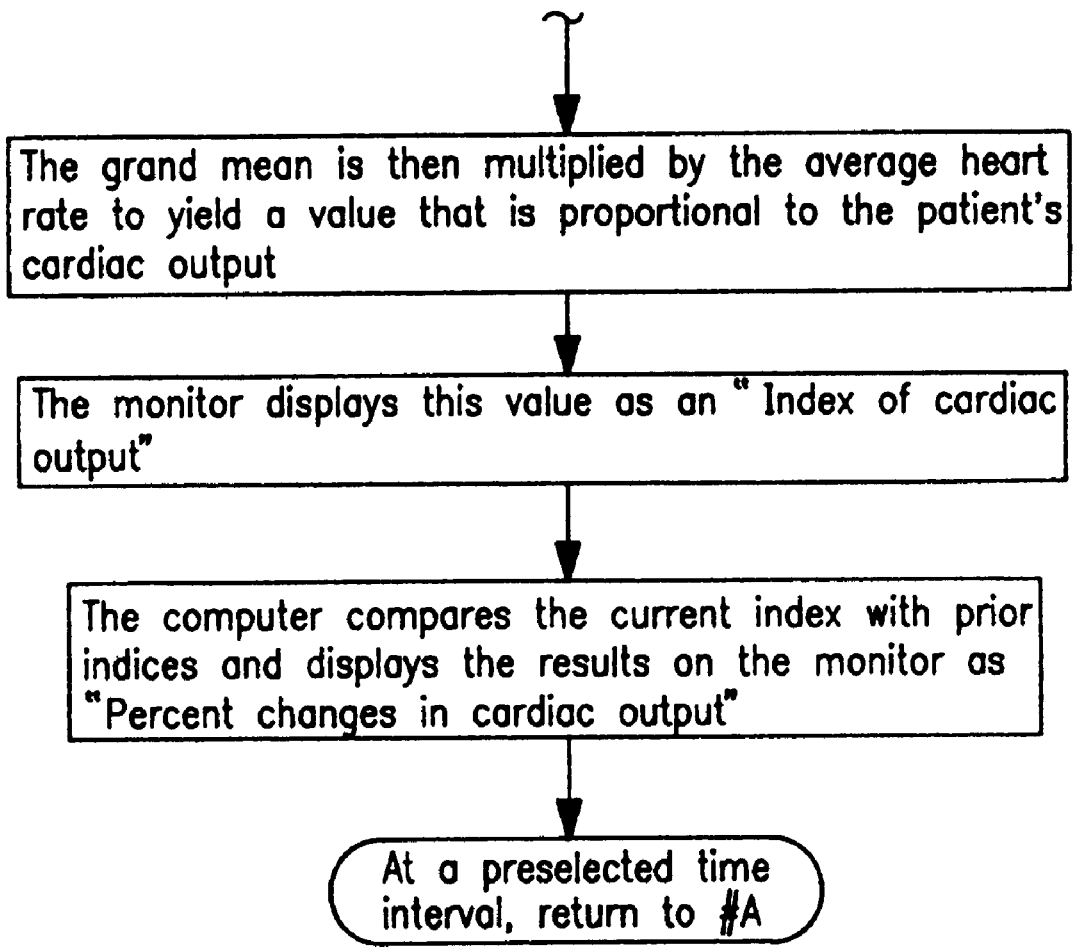

A preferred method for determining an index of cardiac output using the left atrial balloon pressure wave form in accordance with the above discussion is illustrated generally at 680 in the flow chart of FIG. 25.

Figure 15:
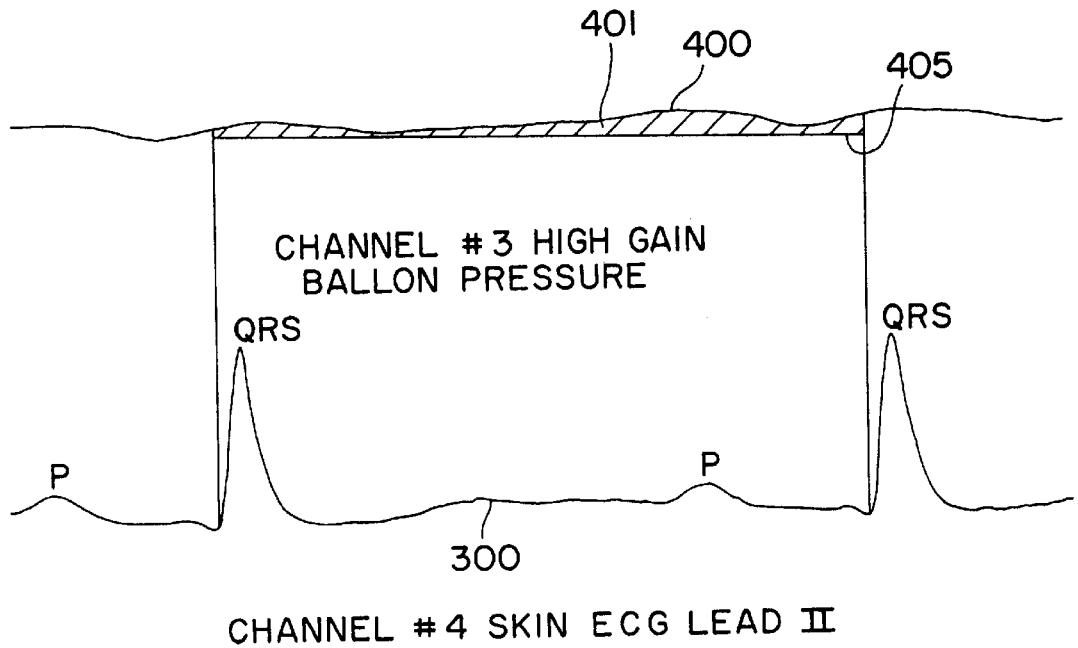
FIGS. 15 and 16 are graphs or tracings, with simultaneous ECGs, of left atrial balloon pressure in a person with leg cuffs restricting blood flow to the legs and with the leg cuffs removed respectively and illustrating the obtaining of an index of cardiac output.
Figure 16:
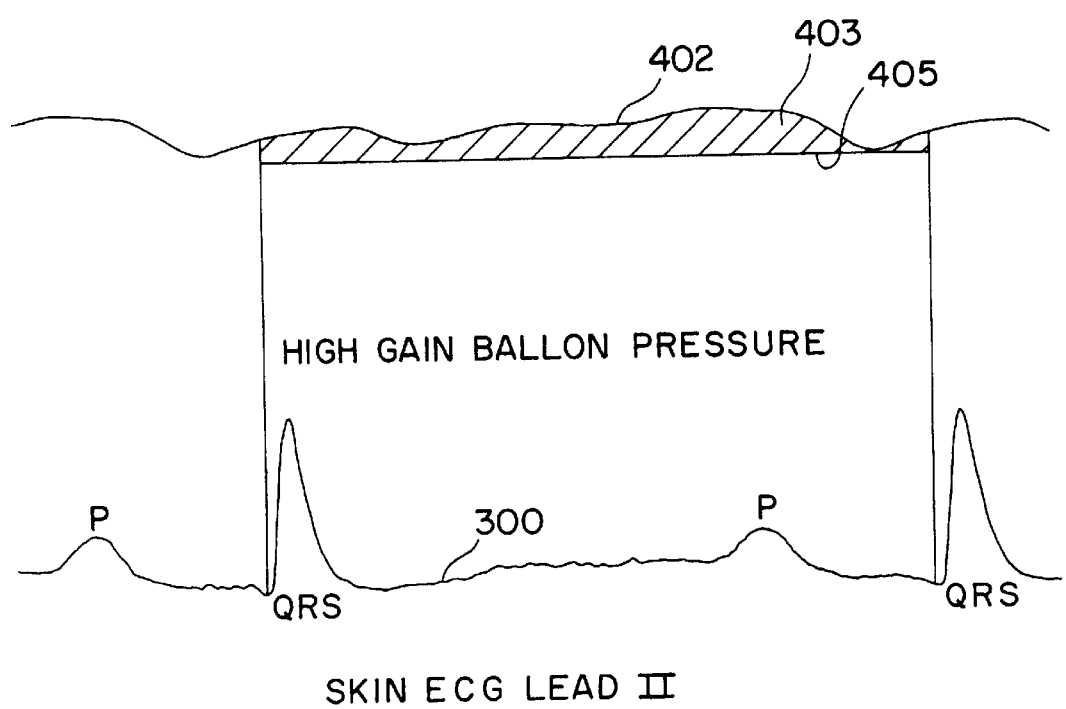

Referring to FIGS. 15 and 16, there are shown at 400 and 402 respectively representative tracings of high gain balloon pressure with the balloon in the esophagus adjacent and under the left atrium of a person, and simultaneous ECGs 300. For each of these tracings 400 and 402, an area, illustrated at 401 and 403 respectively (which areas are hatched for ease of illustration) was defined under the respective curve for the length of a single heartbeat, i.e., from the beginning of one QRS complex to the beginning of the next QRS complex, to a base line, illustrated at 405, which corresponds to the lowest pressure during the cycle. Balloon pressure 400 was taken with leg cuffs restricting blood flow from the legs so that a low cardiac output would be expected. Balloon pressure 402 was taken with the leg cuffs off so that greater cardiac output would be expected. As seen in FIGS. 15 and 16, the area 403 for balloon pressure 402 is greater than area 401 for balloon pressure 400 indicative of greater cardiac output for tracing 402, which is consistent with the leg cuffs being off. By use of impedance cardiography, an increase of 24 percent in cardiac output was measured in the same person (at a different time but under similar conditions) when the leg cuffs were removed, thus confirming the usefulness of the area under an atrial pressure wave form for determining an index of cardiac output.

Figure 18:
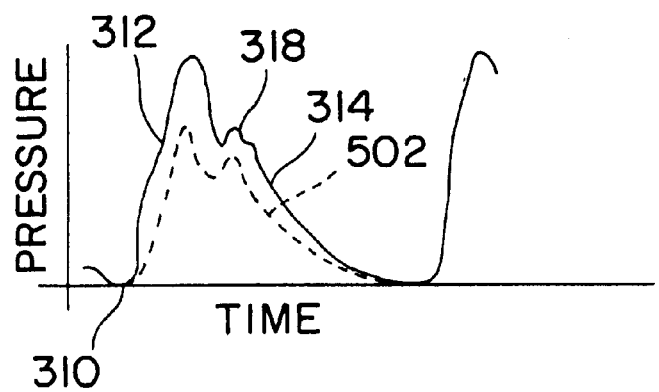
FIG. 18 is an illustration of aortic pressure, illustrating an alternative means of obtaining an index of cardiac output.

Referring to FIG. 18, there is illustrated an alternative means of obtaining an index of cardiac output (referred to herein as a second cardiac output index) utilizing the aortic pressure 314 as sensed by the aortic balloon 28.2 adjacent the aortic arch. This is based on the principle that pressure follows volume in the aorta (and elsewhere in the vascular system), i.e., as the stroke volume (the volume of blood flowing in the aorta during each heart beat) increases, the pressure increases, and as stroke volume decreases, the pressure decreases. FIG. 18 shows the aortic balloon pressure curve inverted, i.e., when the balloon pressure is shown to be increasing, it is actually decreasing. Thus, for analysis purposes, the aortic balloon pressure curve 314 is inverted to properly reflect the pressure within the balloon and tissues adjacent the aortic arch. This is because, in theory, the aortic arch AAR, responding to increased flow in the aorta and therefore increased pressure, will open or tend to straighten (the ascending and descending aorta AA and DA respectively move away from each other) like a Bourdon tube as the pressure rises during systole, and the opening or tendency to straighten of the aortic arch (resulting, with reference to FIG. 6, in the descending aorta DA tending to move away from the aortic balloon 28.2 while the ascending aorta AA remains firmly fixed to the heart) will relieve force acting on the aortic balloon in the esophagus to thus decrease aortic balloon pressure. Similarly, pressure in the aortic balloon will increase when the aortic arch closes as the aortic pressure drops. The observation that the pressure recorded by an esophageal balloon adjacent the aortic arch was inverted with respect to the actual intra-aortic pressure was made by Taquini in 1940. See Taquini, "The Esophageal Pulse Under Normal and Abnormal conditions", *The American Heart Journal*, vol. 40 (no.2), 129–140 (1940).

During systole, the stroke volume is the sum of arterial uptake and systolic runoff or drainage. The arterial uptake is the volume of blood stored in the aorta as a result of distension, this volume being returned to the circulation as diastolic runoff. The arterial uptake acts to increase the aortic blood pressure as previously stated.

Systolic runoff is believed to deflect the aortic arch as a result of Newton's third law of motion acting within the curve of the aortic arch. Thus, blood that is being propelled out and around the aortic arch by the pumping action of the heart exerts a force on the aorta which tends to deflect it. Thus, it is believed that both flow through (systolic runoff) and the arterial uptake may tend to deflect the aortic arch. By inverting the aortic balloon pressure wave form, the wave form 312 is obtainable which is thus considered to be proportional to aortic deflection. This being so, the area under the inverted pressure/time curve 314 of the aortic balloon pressure wave (for one heart beat) may be determined by suitably filtering the signal digitally and integrating, and this area is believed to be proportional to blood flow or stroke volume, i.e., it indicates greater or lesser flow through the aorta as the inverted balloon pressure curve increases or decreases respectively. Thus, this area is believed to provide an index of cardiac output when multiplied by heart rate.

The full line pressure wave 314 is for a higher pressure/flow. The dotted line pressure wave 502 is illustrated for a lower pressure/flow. In accordance with the present invention, the area under the wave, which thus indicates greater or lesser volume flowing through the aorta, is accordingly integrated and multiplied by the heart rate to determine an index of cardiac output.

Figure 20:
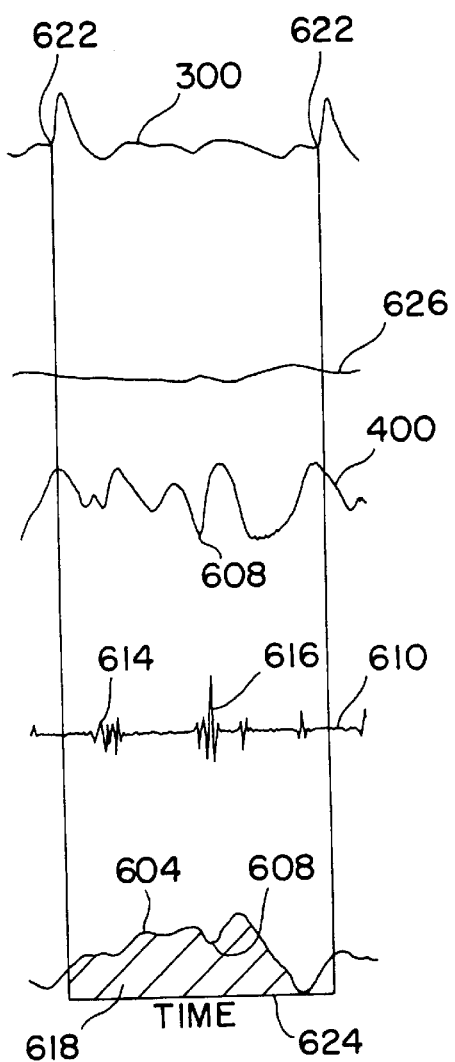
FIGS. 20 and 21 are graphs or tracings, similar to those of FIGS. 15 and 16, with simultaneous ECGs, of aortic balloon pressure in a person with leg cuffs restricting blood flow to the legs and with the leg cuffs removed respectively and illustrating the obtaining of an alternative or second index of cardiac output.
Figure 21:
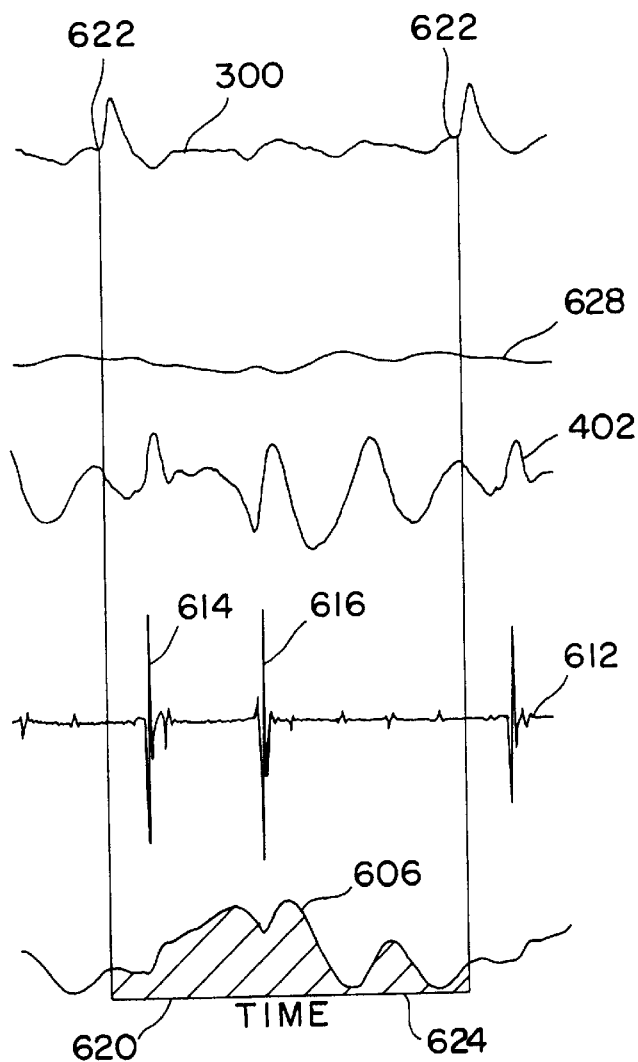
Figure 22A:
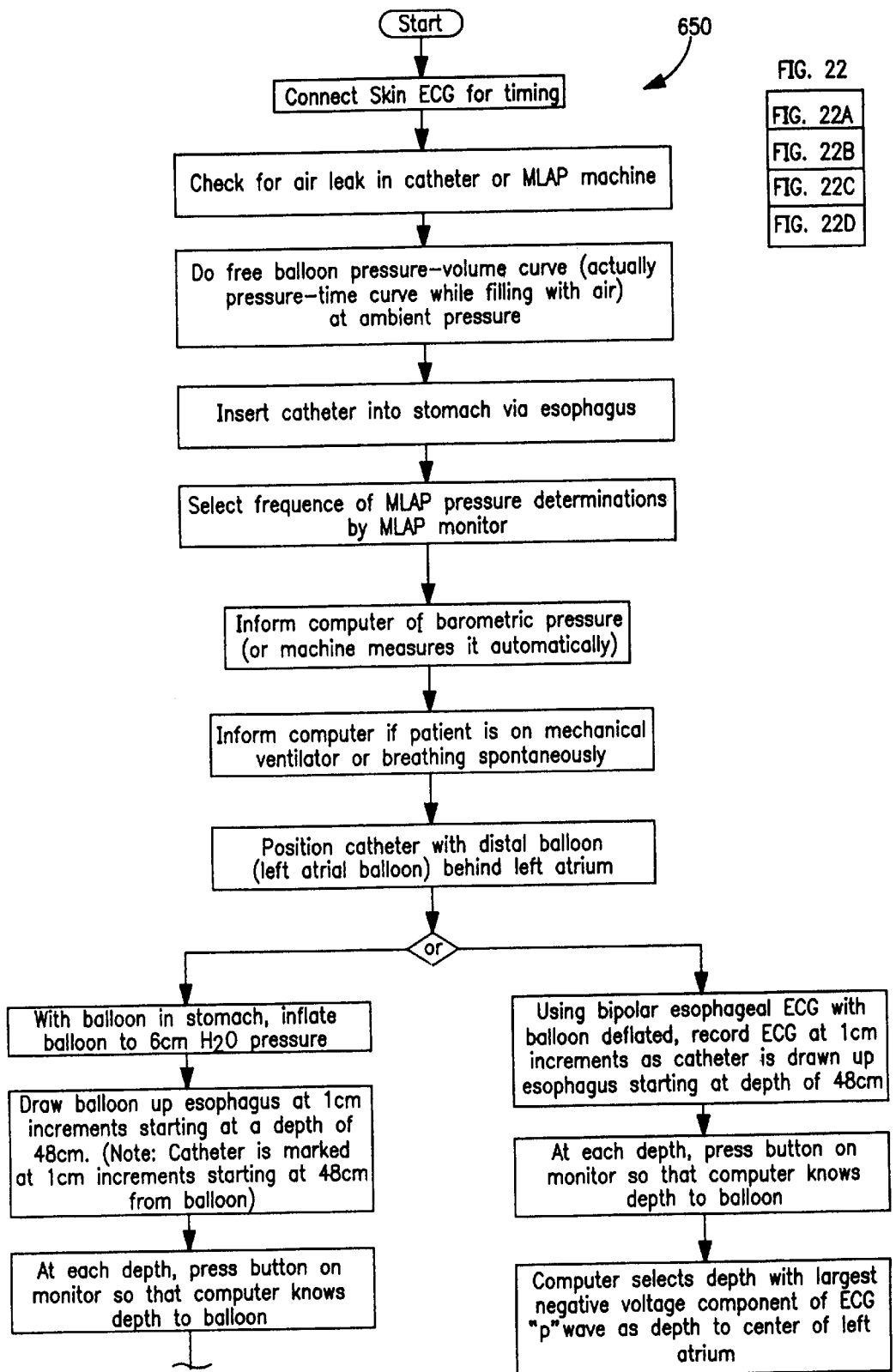
FIG. 22 is a flow chart of a preferred method of determining mean left atrial pressure.
Figure 22B:
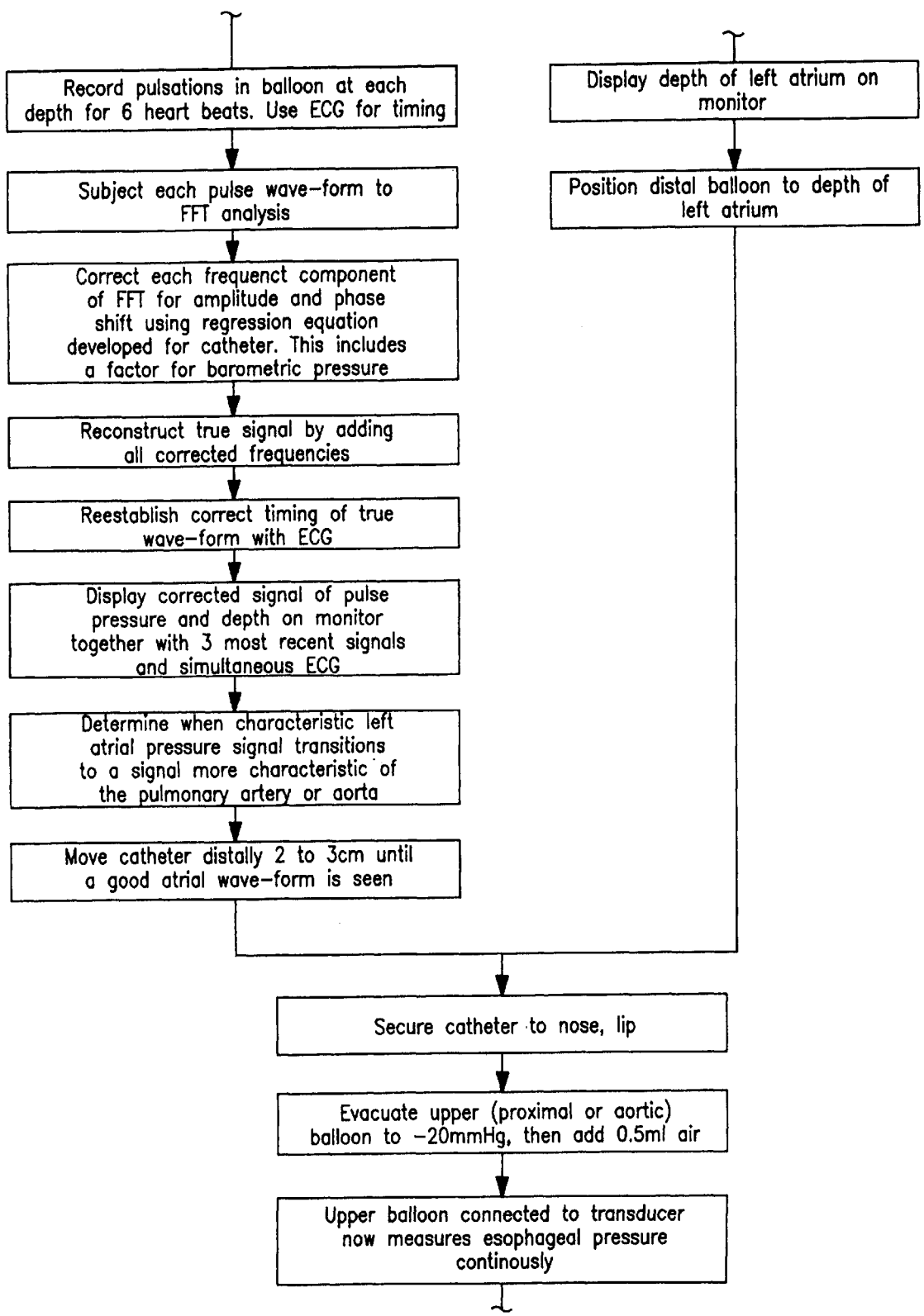
Figure 22C:
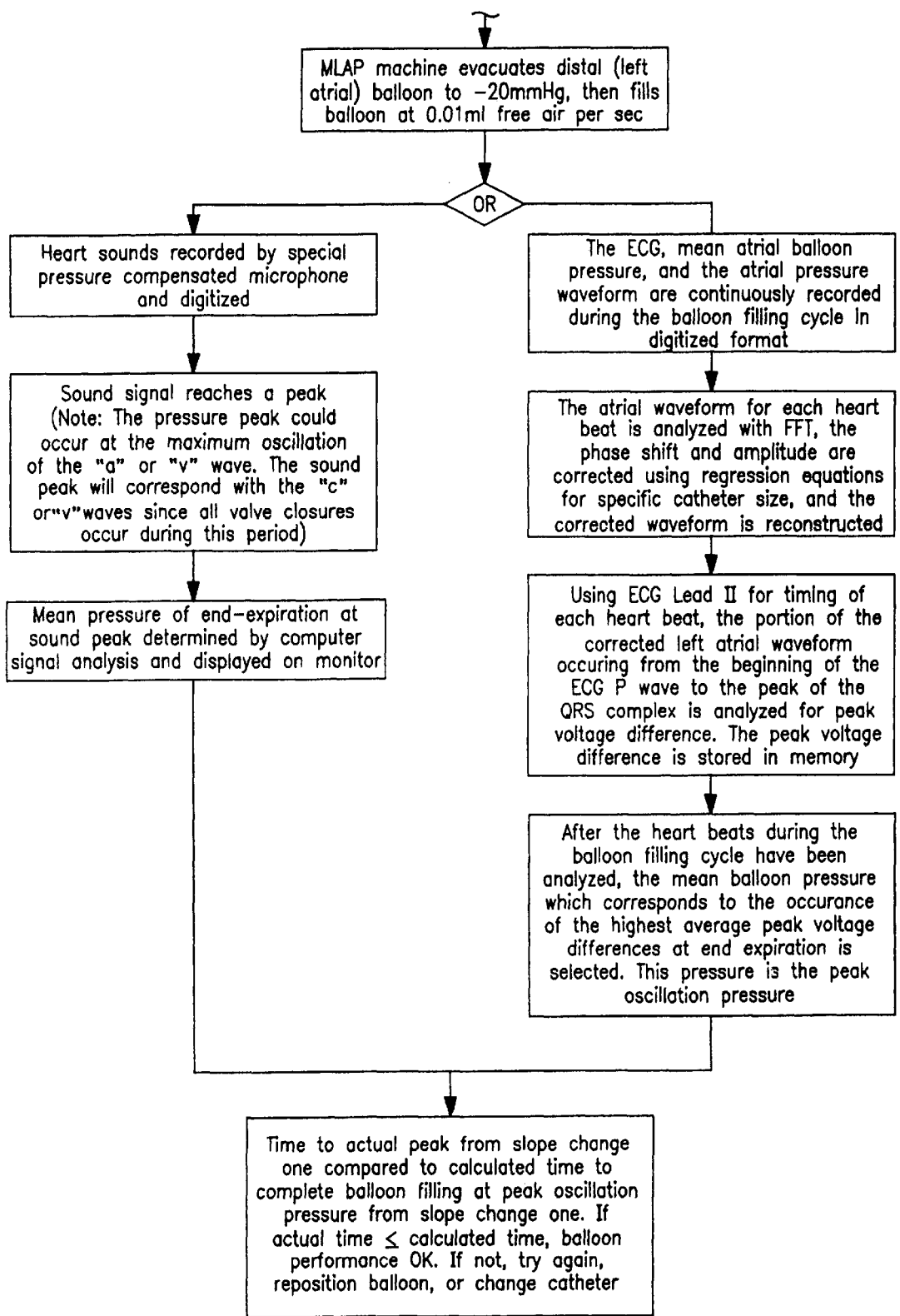
Figure 22D:
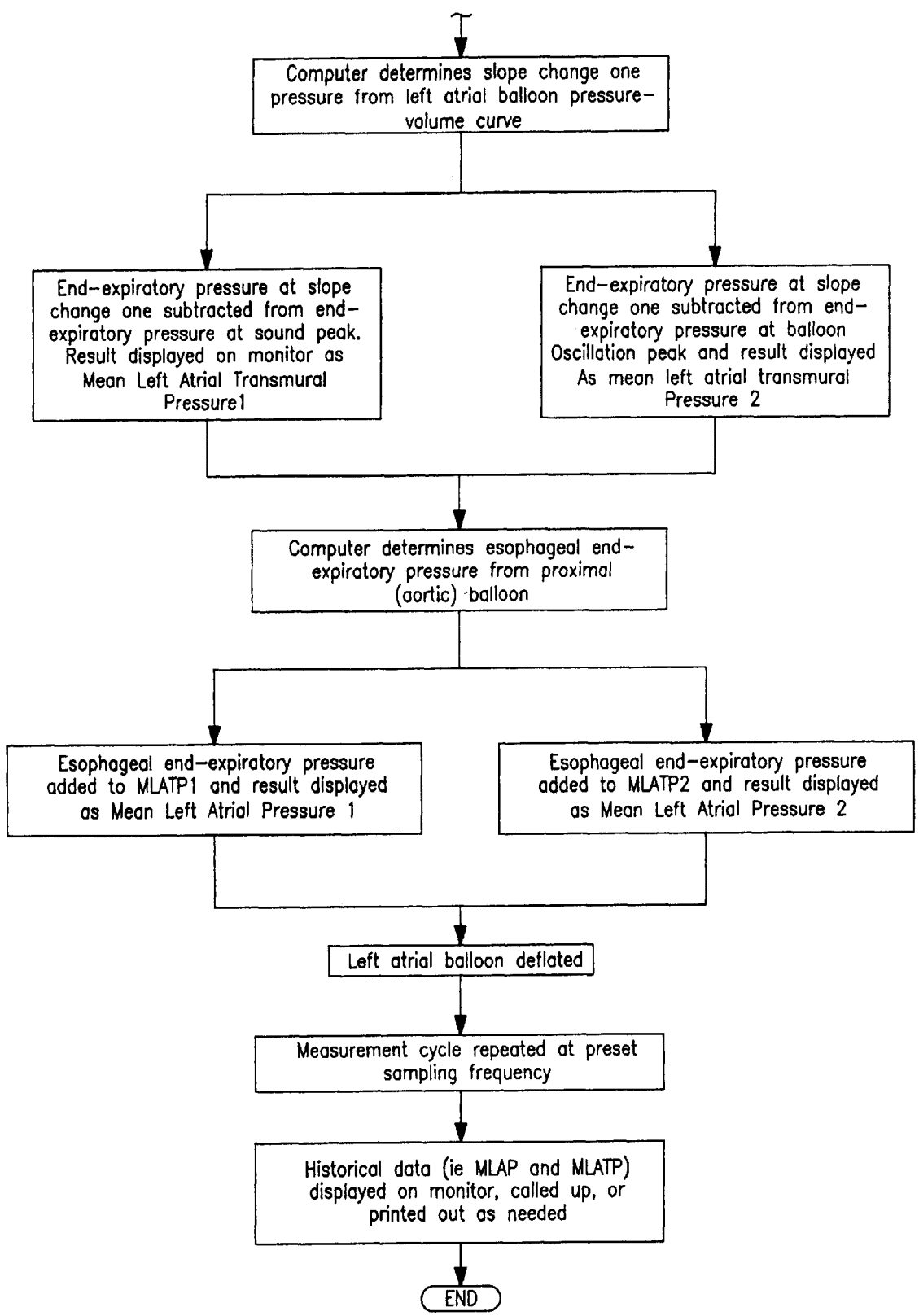
Figure 23A:
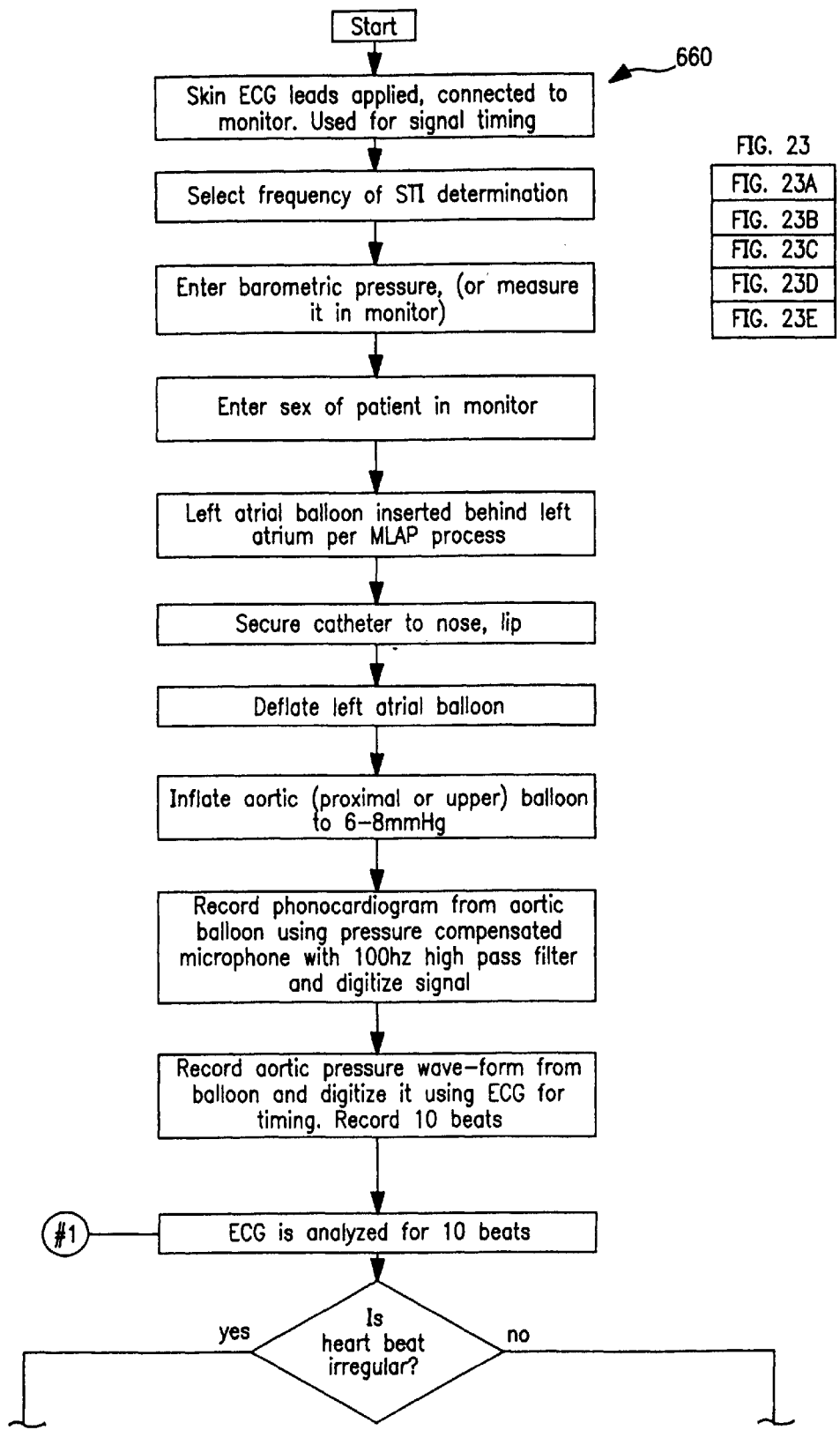
FIG. 23 is a flow chart of a preferred method of determining systolic time intervals and components thereof.
Figure 23B:
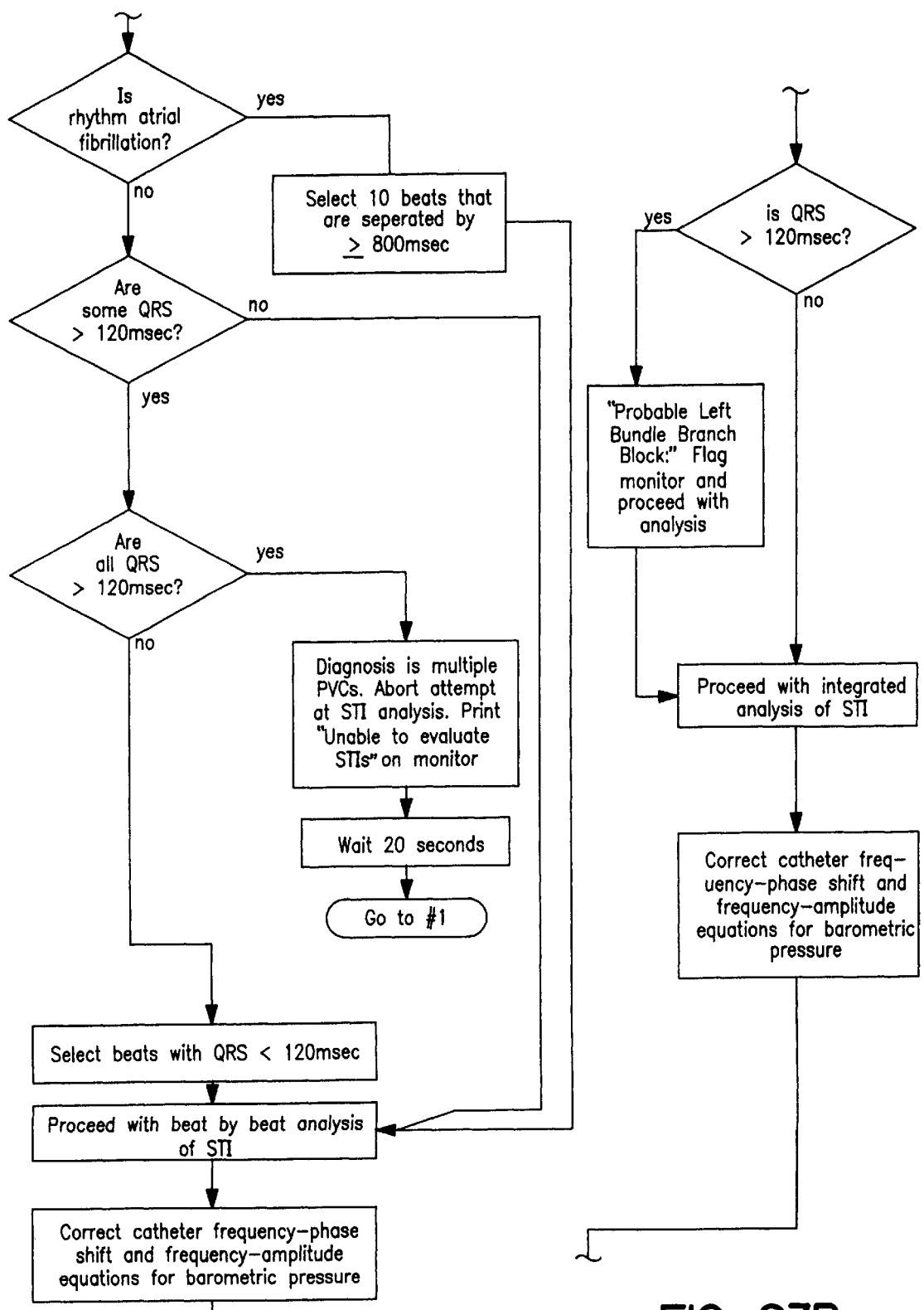
Figure 23C:
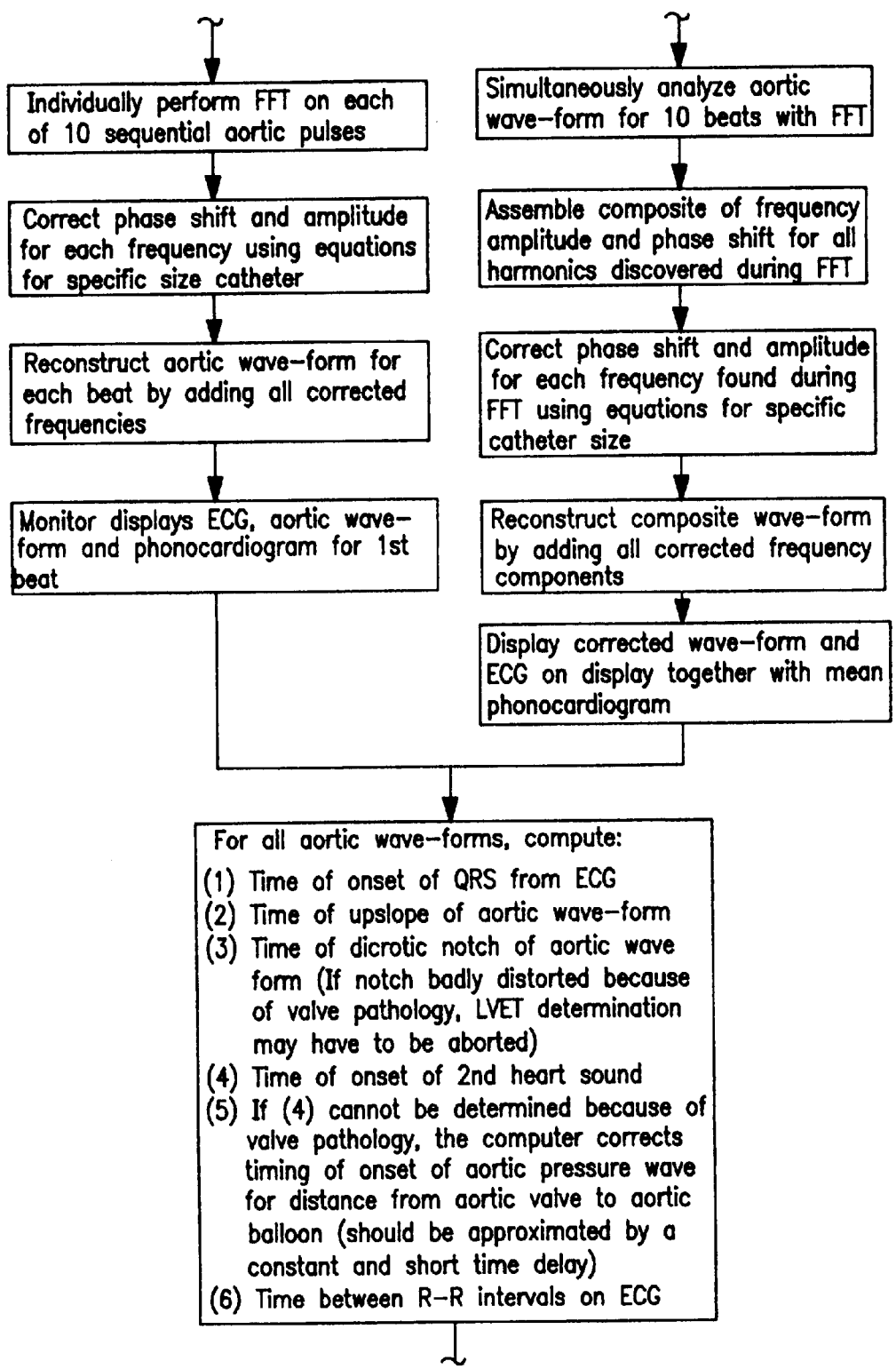
Figure 23D:
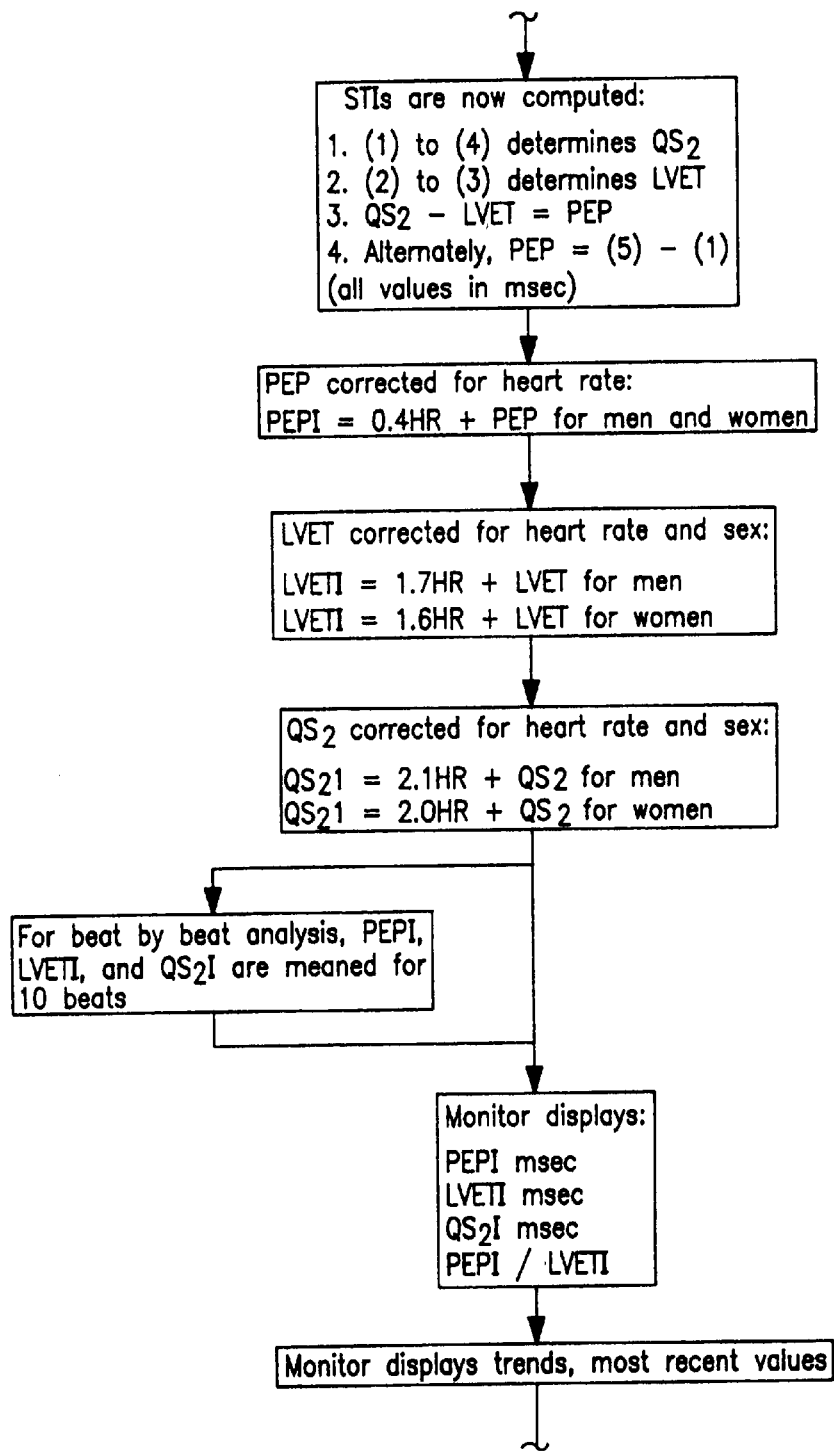
Figure 23E:
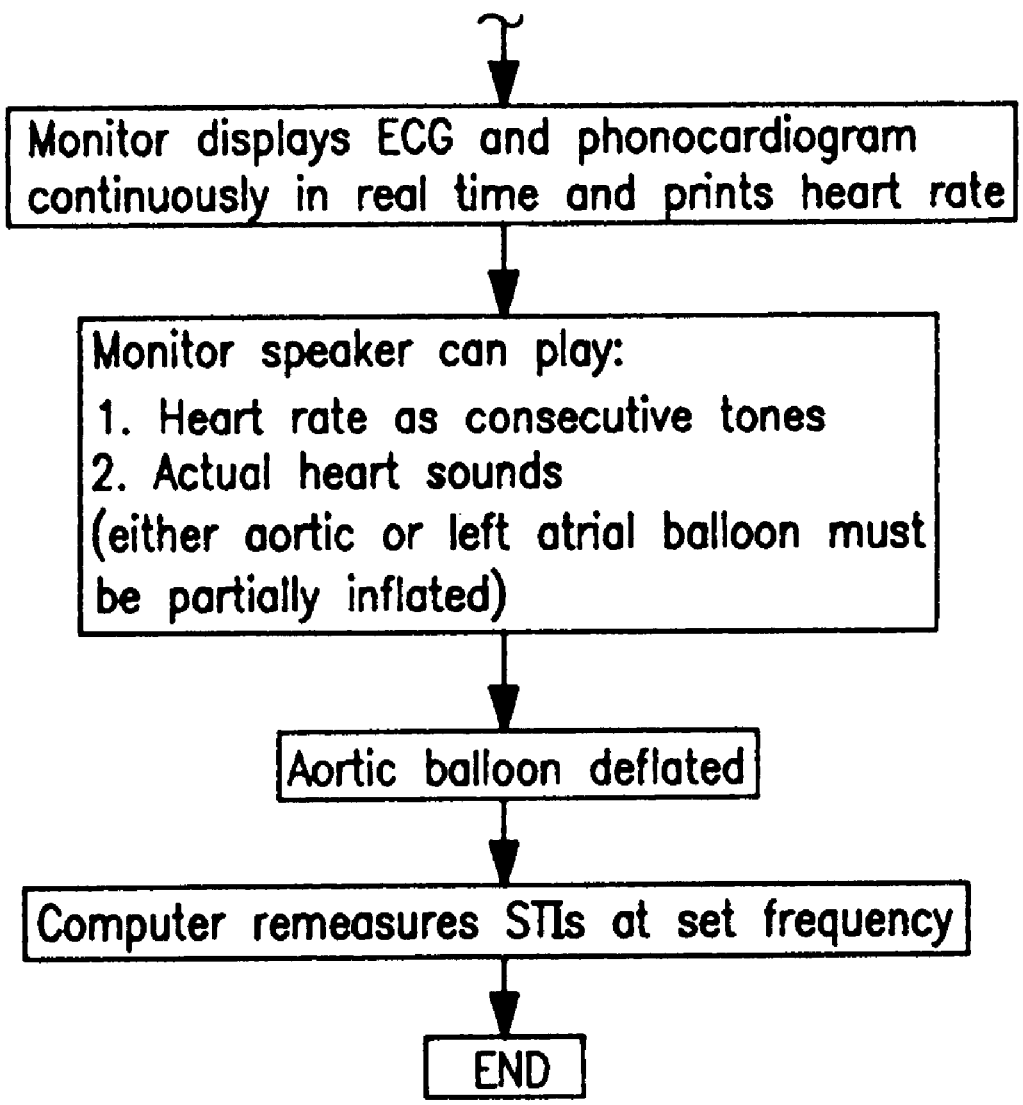

Referring to FIGS. 20 and 21, there are shown at 400 and 402 respectively representative tracings, inverted, of aortic balloon pressure with the balloon in the esophagus adjacent the aortic arch AAR of a person, and simultaneous ECGs 300. Tracings thereof, suitably filtered to remove respiratory excursions, are illustrated at 604 and 606 respectively, and the dicrotic notch is illustrated at 608. Illustrated at 610 and 612 are simultaneous tracings of heart sound recordings respectively, illustrating the first and second heart sounds at 614 and 616 respectively. Illustrated at 626 and 628 are tracings of absolute aortic balloon pressures therefor respectively. The period of the heart beat for tracing 604 is shorter than that of tracing 606 because of irregular heart beat due to atrial flutter. For each of these tracings 604 and 606, an area, illustrated at 618 and 620 respectively (which areas are hatched for ease of illustration) was defined under the respective curve for the length of a single heartbeat, i.e., from the beginning, illustrated at 622, of one QRS complex to the beginning 622 of the next QRS complex, to a base line, illustrated at 624, which corresponds to the lowest pressure during the cycle. Balloon pressure 604 was taken with leg cuffs restricting blood flow from the legs so that a low cardiac output would be expected. Balloon pressure 606 was taken with the leg cuffs off so that greater cardiac output would be expected. As seen in FIGS. 20 and 21, the area 618 for balloon pressure 604 per unit elapsed time is less than area 620 for balloon pressure 606 (despite differences in heart rate) indicative of greater cardiac output for tracing 606, which is consistent with the leg cuffs being off. By use of impedance cardiography, an increase of about 25 percent in cardiac output was measured in the same person (at a different time but under similar conditions) when the leg cuffs were removed, thus confirming the usefulness of the area under an inverted aortic pressure wave form for determining an index of cardiac output.

A preferred process for obtaining the second cardiac output index (using the aortic pressure wave form) includes the following steps:

a. Connect the skin ECG for timing;

b. Check for any air leaks in the catheter or MLAP machine;

c. Insert catheter into the stomach via esophagus;

d. Position catheter with the distal (left atrial) balloon behind the left atrium per "MLAP Process." This automatically positions the aortic (proximal) balloon;

e. Deflate the left atrial balloon;

f. Select the frequency of desired measurement;

g. Evacuate aortic (proximal) balloon to −20 mm Hg;

h. Gradually fill the aortic balloon with air until a slope change of the pressure-time curve is encountered, then stop filling;

i. Add 1.0 ml air to the balloon and close valve. No air is to be added or removed thereafter until measurement is completed;

j. Monitor the pressure from the aortic balloon using the differential transducer and the low-pass filter to remove fluctuating pressure effects from respirations;

k. Invert the pressure waveform to make it appear upright and display on the monitor;

l. Record the aortic balloon pressure waveforms for several heart beats (for example, 6) at end expiration;

m. Using the ECG for timing, correct the pressure waveform for each heart beat using fast Fourier analysis;

n. Calculate the waveform pressure-time integral for each heart beat relative to a baseline that is defined by the lowest pressure seen during each heart beat;

o. Calculate the mean pressure-time integral by summing all 6 pressure-time integrals and dividing by 6;

p. Calculate the average heart rate that occurred while measuring the 6 aortic pressure signals using the ECG;

q. Multiply the mean pressure-time integral by the average heart rate. This number is an index of cardiac output;

r. Display the index of cardiac output on the monitor and store it together with the date and time for future reference;

s. The computer compares the current index of cardiac output with prior indices and displays the results on the monitor as percent changes in cardiac output";

t. At a preselected time interval, return to step F.

Preferably, while the wave forms (left atrial or aortic) are being evaluated on the monitor, or perhaps on chart paper from the recorder 16, the information processing means will collect, for example, six (6) pressure cycles (preferably at end expiration) and corresponding ECGs and will digitize them. The processor 12 is suitably programmed to establish for each wave form a base line corresponding to the lowest pressure observed during the respective heartbeat. The pressure-time integrals are then calculated, summed, and then divided by the number of wave forms to yield a mean value. This mean value is then multiplied by the average heart rate that occurred during the measurements (from analyzing the ECG). This yields an individual index of cardiac output which may then be compared with subsequent or prior indexes to determine whether cardiac output is increasing, decreasing, or remaining constant.

If it is determined that the mitral valve is damaged, the resulting back-flow may invalidate the use of the left atrial pressure wave for obtaining an index of cardiac output, it is preferred in this circumstance to obtain an index of cardiac output using the aortic balloon and aortic pressure wave form (which would not be affected by such back-flow).

The above procedures for obtaining an index of cardiac output may work well for people with various heart conditions such as atrial flutter.

While preferably an area under an aortic or left atrial wave form may be suitably processed and integrated and multiplied by heart rate to obtain an index of cardiac output, FIGS. 15 and 16 illustrate that such a precise analysis may not be necessary in all situations since the differences in area may often be merely eye-balled to give health care personnel the information needed to determine whether a patient's cardiac output is increasing or decreasing or staying the same.

Alternatively, slopes of certain segments of the left atrial and aortic pressure wave forms may be measured to provide an index of cardiac output. However, it is believed that the area under an aortic or left atrial pressure wave, being more comprehensive, provides a more reliable index of cardiac output.

Measuring Pulse Wave Velocity

Pulse wave velocity can be used as an index of arterial rigidity. In order to determine pulse wave velocity, in accordance with the present invention, the distance between the aortic arch and an other artery is divided by the time difference between the pulse at the aortic arch and the pulse at the other artery for the same heartbeat. Thus, the pressure wave form from the aorta is compared with the pressure wave form from another artery.

Figure 19:
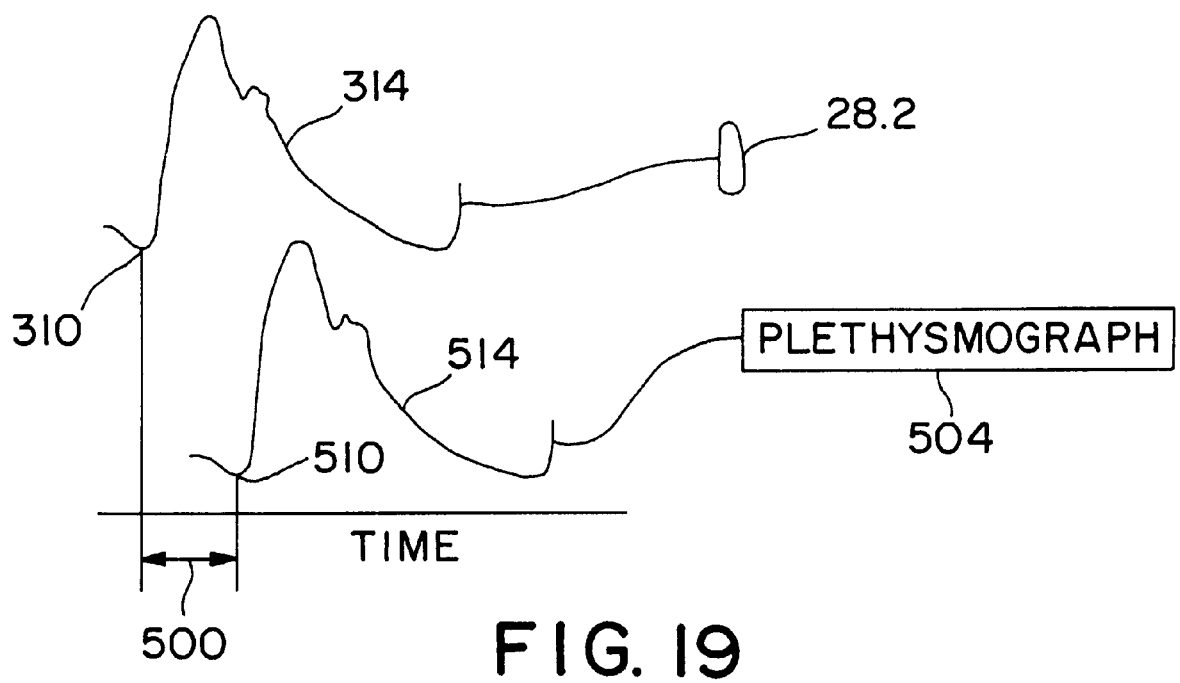
FIG. 19 is an illustration of aortic pressures taken at the aortic arch and carotid artery respectively, illustrating a means of determining pulse wave velocity.

Accordingly, an esophageal balloon is positioned next to the aortic arch, and a point on the pressure wave from the balloon, after being suitably corrected by fast Fourier transform analysis, is compared with the corresponding point on the pressure wave from the carotid (or other suitable) artery which may be picked up by a plethysmograph or by a low frequency microphone or otherwise suitably picked up. The aortic wave may be used to determine the pulse wave velocity by determining the onset of the pulse wave (indicative of opening of the aortic valve) at, for example, the aortic arch and at another suitable artery, for example, the carotid artery, determining the difference in time and distance there between and deriving therefrom the velocity by dividing the distance by the time in accordance with conventional principles. As the artery becomes more rigid, the pulse wave velocity generally increases. Thus, the pulse wave velocity may be used as an index of artery rigidity, and stroke volume capacity may also be inferred therefrom. Referring to FIG. 19, in order to provide means for easily and reliably determining pulse wave velocity which can be used by paramedical personnel with minimal training, in accordance with the present invention, the aortic pressure wave form 314 provided by the aortic balloon 28.2 adjacent the aortic arch is suitably corrected by fast Fourier analysis, in accordance with principles commonly known to those of ordinary skill in the art to which this invention pertains. Preferably, the time period between onsets 310 and 510 of the aortic balloon and carotid (or other) artery signals respectively are determined since the wave tends to become distorted (becomes narrower and higher) with increased distance from the aortic arch. Thus, the time period, illustrated at 500, between the corrected time 310 of onset of the aortic balloon signal 314 and the time 510 of onset of the carotid artery signal 514 of the pulse wave as taken by a plethysmograph 504 is suitably calculated, using principles commonly known to those of ordinary skill in the art to which this invention pertains, and the pulse wave velocity, an index of artery rigidity, derived therefrom as previously discussed.

A preferred process for measuring pulse wave velocity includes the following steps:

a. Connect a skin ECG for timing;

b. Check for air leak in the catheter or MLAP machine;

c. Insert the catheter into stomach via the esophagus;

d. Position the catheter with the distal (left atrial) balloon behind the left atrium per the "MLAP Process", which will automatically position the proximal (aortic) balloon;

e. Deflate the left atrial balloon;

f. Select the frequency of the desired measurement;

g. Evacuate the aortic (proximal) balloon to −20 mm Hg;

h. Gradually fill the aortic balloon with air until a slope change of the pressure-time curve is encountered, then stop filling;

i. Add 1.0 ml air to the balloon and close valve. No air is to be added or removed thereafter until the measurement is completed;

j. Monitor the pressure from the aortic balloon using a differential transducer and low-pass filter to remove fluctuating pressure effects from respirations;

k. Invert the aortic balloon signal to make it appear upright;

l. Attach a plethysmograph or low frequency (<100 Hz) phonocardiograph pick-up over peripheral artery (e.g., carotid, radial, femoral);

m. Measure the distance from the selected peripheral artery on the body surface to the aortic arch (which is at the level of the sternal angle of Louis where the second rib joins the sternum) and enter this distance into the computer;

n. Simultaneously record the aortic pulse from the catheter and the peripheral pulse from the plethysmograph or phonocardiograph;

o. Using the ECG for timing, perform fast Fourier transform analysis and reconstruction to correct the aortic pulse signal for phase shift and amplitude;

p. Compute the time difference between the corrected aortic pulse and the peripheral pulse;

q. Divide the distance between the aortic and peripheral pulses by the time difference to determine pulse wave velocity;

r. Display the pulse wave velocity on the monitor and record in memory;

s. At a preselected time interval, repeat steps f to r.

Determining Left Ventricular Contractility Index

It is recognized that the contractility index is a sensitive indicator of cardiac performance. The present apparatus may be used to provide such an index by computing (dp/dt/MLAP), dp being the diastolic pressure less the mean left atrial pressure, and dt being PEP. To this end, the patient P is connected to the ECG electrodes as shown in FIG. 1 and to an automatic blood pressure device 22, also as shown in FIG. 1. (While use of an automatic blood pressure device is the preferred manner for determining blood pressure, other ways may be used to determine blood pressure, such as, for example, by arterial pressure transducers.) After the ECG electrodes have been properly connected, the catheter 20 is inserted into the esophagus in accordance with the procedures set forth above to properly position the left atrial balloon 28.1 behind the left atrium. With the foregoing equipment attached to the information processing means 12, the frequency of desired measurements is entered into the processing means 12. The mean left atrial pressure is determined in accordance with the procedure discussed above. The actual pre-ejection time period (PEP) is determined in accordance with the procedure discussed above, this being equal to "dt" in the equation set forth above. From the blood pressure device, diastolic blood pressure is determined, and MLAP is subtracted from diastolic blood pressure to give the "dp" of the equation set forth above. It is now necessary to only solve the equation and to display the result, an approximation of the index of contractility, on the monitor.

A preferred process for determining a left ventricular contractility index includes the following steps:

a. Insert the left atrial balloon behind the left atrium in accordance with the MLAP process, as illustrated in FIG. 22.

b. Attach skin ECG electrodes.

c. Connect to output of automatic blood pressure device (or arterial pressure transducer) or manually input diastolic pressure.

d. Enter the frequency of desired measurements.

e. Using the MLAP process of FIG. 22, determine the MLAP.

f. Using the STI process of FIG. 23, determine the actual PEP, which equals dt.

g. From the blood pressure device or manual input, retrieve the diastolic blood pressure.

h. Subtract MLAP from the diastolic blood pressure, thereby obtaining dp.

i. Calculate from the above dp/dt/MLAP.

j. Display the result on the monitor.

k. Repeat steps e to j until the desired number of measurements is reached.

Other Cardiac Performance Determinations

As discussed above, the catheter 20 and its associated pressurizing and monitoring equipment along with a standard ECG and blood pressure cuff may be used to inexpensively yet reliably, conveniently, and noninvasively obtain various cardiac performance parameters. The apparatus of the present invention may also include a phonocardiograph for use in obtaining systolic time intervals, as previously discussed, and an automatic blood pressure cuff for continuously monitoring systolic and diastolic blood pressures, which are useful in that the systolic pressure shows the peak pressure that the ventricle can generate while the diastolic pressure is the minimum pressure which the heart has to overcome to cause blood to flow. In addition to a phonocardiograph for the aortic balloon, a phonocardiograph is also provided for the atrial balloon so that the function of the mitral and aortic heart valves may be analyzed with respect to leakage and resistance to flow.

Thus, the noninvasive apparatus of the present invention is provided, without the need for additional pieces of apparatus which may be expensive or invasive, to inexpensively yet reliably and continuously obtain determinations of major cardiac performance parameters as follows:

mean left atrial pressure to determine the priming pressure of the left ventricle heart valve function analysis, which addresses a problem in the practice of anesthesia wherein changes in heart sound or rhythm need to be recognized immediately.

electrographic analysis of the heart's beating frequency and rhythm systolic time intervals including the ratio PEP/LVET mean left atrial transmural pressure as an index of left atrial filling pressure unbiased by thoracic pressure changes such as may be caused, for example, by a mechanical ventilator systolic and diastolic blood pressures the left ventricular contractility index two alternative indices of cardiac output pulse wave velocity the determination of pulse amplitude ratios before, during, and after the Valsalva maneuver Esophageal pressure (an established estimate of pulmonary pleural pressure), which can be used in conjunction with other pulmonary measurements to determine (a) the elastic properties of the lungs, (b) lung isovolume pressure-flow curves, (c) the work of breathing, and (d) pressure stacking or intrinsic positive end expiratory pressure.

The distal and proximal balloons and their spatial relation on the catheter, as hereinbefore discussed, advantageously allows one standard catheter to fit virtually all adults and advantageously allows this standard catheter to be easily and conveniently positioned just once for reliably obtaining the pressures and sounds in order to determine the various cardiac performance parameters listed above.

Statements of theory are contained herein to aid in understanding of the invention. Although such statements of theory are believed to be correct, applicant does not wish to be bound by them.

While the best mode of this invention known to applicant at this time has been shown in the accompanying drawings and described in the accompanying text, it should be understood that applicant does not intend to be limited to the particular details illustrated in the accompanying drawings and described above. Thus, it is the desire of the inventor of the present invention that it be clearly understood that the embodiments of the invention, while preferred, can be readily changed and altered by one skilled in the art and that these embodiments are not to be limiting or constraining on the form or benefits of the invention.

What is claimed is:

1. A method for obtaining an index of cardiac output of a person which may be done noninvasively by paramedical personnel, the method comprising the following steps: providing an esophageal catheter having at least one balloon; inserting into the esophagus of the person the catheter and positioning the balloon in a position adjacent the left atrium to sense left atrial pressure; pressurizing the balloon; and utilizing effects of left atrial pressure on the pressurized balloon to obtain a wave form of left atrial pressure; determining an area between the left atrial pressure wave form and a baseline for each of a plurality of heartbeats; adding the areas and dividing by the number of heartbeats to obtain an average; and multiplying the average by the heart rate of the person to obtain an index for comparison with another such index.

2. A method for determining cardiac performance of a person which may be done noninvasively by paramedical personnel, the method comprising the following steps: providing an esophageal catheter having at least one balloon; inserting into the esophagus of the person the catheter and positioning the balloon in a position adjacent the left atrium to sense left atrial pressure; pressurizing the balloon; and utilizing effects of left atrial pressure on the pressurized balloon to determine at least one cardiac performance parameter, the step of positioning the balloon comprises inflating the balloon, gradually pulling the catheter up the esophagus while observing pressure wave forms generated by the balloon, and, when the pressure wave forms transition from a characteristic left atrial pressure wave form to a pressure wave form more characteristic of the pressure wave form of the pulmonary artery or aorta, moving the catheter downwardly about 2 to 3 centimeters until a left atrial pressure wave form is seen.

3. A method of determining mean left atrial transmural pressure comprising the steps of: inserting into the esophagus a catheter having a balloon; positioning the balloon adjacent the left atrium to sense left atrial pressure; pressurizing the balloon; measuring balloon pressure when portions of the balloon pressure wave form corresponding to the "a" wave portions of the left atrial pressure wave are at a peak; subtracting from the balloon pressure the pressure at an abrupt balloon pressure slope change from a fast to a slowed rate of balloon pressure increase indicative of equalization of balloon pressure with surrounding tissue pressure prior to balloon expansion to determine mean left atrial transmural pressure.

4. A method of determining mean left atrial transmural pressure comprising the steps of: inserting into the esophagus a catheter having a balloon; positioning the balloon adjacent the left atrium to sense left atrial pressure; pressurizing the balloon; obtaining a signal corresponding to the balloon pressure; differentiating the signal using a differentiator; measuring balloon pressure when the amplitude of oscillations of the differentiated balloon pressure signal is at a peak; subtracting from the measured balloon pressure the pressure at an abrupt balloon pressure slope change from a fast to a slowed rate of balloon pressure increase indicative of equalization of balloon pressure with surrounding tissue pressure prior to balloon expansion to determine mean left atrial transmural pressure.

5. A method according to claim 4 wherein the step of measuring balloon pressure is performed during the period of time of each heartbeat from the beginning of the wave until the peak of the QRS complex on a ECG.

* * * * *

UNITED STATES PATENT AND TRADEMARK OFFICE
CERTIFICATE OF CORRECTION

PATENT NO. : 6,238,349 B1  
DATED : May 29, 2001  
INVENTOR(S) : Donald D. Hickey Page 1 of 1

It is certified that error appears in the above-identified patent and that said Letters Patent is hereby corrected as shown below:

<u>Column 24, claim 5,</u>  
Line 3, change "wave" to -- P wave --.

Signed and Sealed this

Twenty-sixth Day of March, 2002

Attest:

Attesting Officer

JAMES E. ROGAN  
*Director of the United States Patent and Trademark Office*